US010253071B2

(12) United States Patent
Cummings et al.

(10) Patent No.: US 10,253,071 B2
(45) Date of Patent: Apr. 9, 2019

(54) SELECTIN INHIBITORS, COMPOSITION, AND USES RELATED THERETO

(71) Applicants:Beth Israel Deaconess Medical Center, Inc., Boston, MA (US); Emory University, Atlanta, GA (US)

(72) Inventors: Richard D. Cummings, Atlanta, GA (US); Elliot L. Chaikof, Newton, MA (US); Venkata R. Krishnamurthy, Ashland, MA (US); Mohammed Sardar, Malden, MA (US)

(73) Assignees: Beth Israel Deaconess Medical Center, Inc., Boston, MA (US); Emory University, Atlanta, GA (US)

( * ) Notice: Subject to any disclaimer, the term of this patent is extended or adjusted under 35 U.S.C. 154(b) by 20 days.

(21) Appl. No.: 14/895,606

(22) PCT Filed: May 23, 2014

(86) PCT No.: PCT/US2014/039308
§ 371 (c)(1),
(2) Date: Dec. 3, 2015

(87) PCT Pub. No.: WO2014/197223
PCT Pub. Date: Dec. 11, 2014

(65) Prior Publication Data
US 2016/0108092 A1      Apr. 21, 2016

(51) Int. Cl.
*C07K 9/00* (2006.01)
*C07K 7/08* (2006.01)
(Continued)

(52) U.S. Cl.
CPC ............... *C07K 9/00* (2013.01); *C07K 7/08* (2013.01); *C07K 14/70564* (2013.01); *A61K 38/00* (2013.01)

(58) Field of Classification Search
CPC ...... A61K 38/00; A61K 31/715; A61K 47/64; A61K 47/6939; A61K 8/73; C07K 16/28;
(Continued)

(56) References Cited

U.S. PATENT DOCUMENTS

| 5,858,994 A | 1/1999 | Kretzschmar |
| 6,136,790 A | 10/2000 | Toepfer |

(Continued)

FOREIGN PATENT DOCUMENTS

| WO | 1999065712 | 12/1999 |
| WO | 2003032925 | 4/2003 |

OTHER PUBLICATIONS

Pudelko et al. Chemical and Chemoenzymatic Synthesis of Glycopeptide Selectin Ligands Containing Sialyl Lewis X Structures. ChemBioChem 2010, 11, 904-930.*

(Continued)

*Primary Examiner* — Marcela M Cordero Garcia
*Assistant Examiner* — Jia-Hai Lee
(74) *Attorney, Agent, or Firm* — Wolf, Greenfield & Sacks, P.C.

(57) ABSTRACT

This disclosure relates to selectin inhibitors, compositions, and methods related thereto. In certain embodiments, the disclosure relates to glycopeptides that contain one more modified amino acids conjugated to a saccharide or polysaccharide. In certain embodiments, the disclosure relates to uses of the glycopeptides as anti-inflammatory, anti-thrombotic, or anti-metastatic agents.

24 Claims, 8 Drawing Sheets

Specification includes a Sequence Listing.

(51) Int. Cl.
  *C07K 14/705* (2006.01)
  *A61K 38/00* (2006.01)
(58) Field of Classification Search
  CPC ............ C07K 2317/41; C12N 15/1138; C12N 2533/70
  See application file for complete search history.

(56) References Cited

U.S. PATENT DOCUMENTS

| | | | |
|---|---|---|---|
| 7,189,828 B2 * | 3/2007 | Cummings | ............ A61K 38/08 424/9.1 |
| 7,223,845 B2 * | 5/2007 | Cummings | ............ C07K 9/00 530/322 |
| 2002/0026033 A1 | 2/2002 | Cummings | |
| 2013/0136741 A1 | 5/2013 | Shaw | |

OTHER PUBLICATIONS

Roosenburg et al. Bioconjug Chem. Stabilized (111)in-labeled sCCK8 analogues for targeting CCK2-receptor positive tumors: synthesis and evaluation. Apr. 21, 2010;21(4):663-70. (Year: 2010).*

Sako et al. A sulfated peptide segment at the amino terminus of PSGL-1 is critical for P-selectin binding. Cell. Oct. 20, 1995;83(2): 323-31. (Year: 1995).*

Ali et al. Trichloroethyl Group As a Protecting Group for Sulfonates and Its Application to the Synthesis of a Disulfonate Analog of the Tyrosine Sulfated PSGL-143-50 Peptide. J. Org. Chem. 2009, 74, 3583-3586. (Year: 2009).*

Baumann et al. Sulfated and Non-Sulfated Glycopeptide Recognition Domains of P-Selectin Glycoprotein Ligand 1 and their Binding to P- and E-Selectin, Angew. Chem. Int. Ed. 2009,48,3174-3178.

Bernimoulin et al. Molecular Basis of Leukocyte Rolling on PSGL-1, The Journal of Biological Chemistry vol. 278, No. 1, pp. 37-47, 2003.

Culmer et al. Circulating and vein wall P-selectin promote venous thrombogenesis during aging in a rodent model, Thrombosis Research 131 (2013) 42-48.

Hicks et al. GLycosulfopeptides modeled on P-selectin glycoprotein ligand-1 inhibit P-selectin-dependent leukocyte roiling in vivo, FASEB J, 2002.

Krishnamurthy et al. Synthesis of an Fmoc-threonine bearing core-2 glycan: A building block for PSGL-1 via Fmoc-assisted solid-phase peptide synthesis, Carbohydr Res. 2010, 345(11): 1541-1547.

Krishnamurthy et al. Glycopeptide analogues of PSGL-1 inhibit P-selectin in vitro and in vivo, Nat Commun. 2015, 6:6387.

Leppanen et al. A Novel Glycosulfopeptide Binds to P-selectin and Inhibits Leukocyte Adhesion to P-selectin, The Journal of Biological Chemistry vol. 274, No. 35, pp. 24838-24848, 1999.

Leppanen et al. Human L-selectin preferentially binds synthetic glycosulfopeptides modeled after endoglycan and containing tyrosine sulfate residues and sialyl Lewis x in core 2 O-glycans, Glycobiology vol. 20 No. 9 pp. 1170-1185, 2010.

Myers et al. Decreased venous thrombosis with an oral inhibitor of P selectin, J Vasc Surg. Aug. 2005;42(2):329-36.

NCBI Reference Sequence: XP_002798811.1 376 aa linear PRI Jun. 1, 2010 Definition Predicted: p-selectin glycoprotein ligand 1-like [Macaca mulatta].

Ohta et al. Inhibition of P-selectin specific cell adhesion by a low molecular weight, non-carbohydrate compound, KF38789, Inflamm. res. 50 (2001) 544-551.

Patel et al. Targeting P-selectin glycoprotein ligand-1/P-selectin interactions as a novel therapy for metabolic syndrome, Transl Res 183, 1-13. 2016.

Watz et al. Inhaled pan-selectin antagonist Bimosiamose attenuates airway inflammation in COPD, Pulmonary Pharmacology & Therapeutics 26 (2013) 265e270.

* cited by examiner

SEQUENCE LISTING

```
<160> NUMBER OF SEQ ID NOS: 12

<210> SEQ ID NO 1
<211> LENGTH: 12
<212> TYPE: PRT
<213> ORGANISM: Homo sapiens
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(5)
<223> OTHER INFORMATION: Xaa can be any naturally occurring amino acid
<220> FEATURE:
<221> NAME/KEY: misc_feature
<222> LOCATION: (7)..(9)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa is proline or hydroxyproline
<220> FEATURE:
<221> NAME/KEY: misc_feature
<222> LOCATION: (11)..(11)
<223> OTHER INFORMATION: Xaa can be any naturally occurring amino acid

<400> SEQUENCE: 1

Tyr Xaa Tyr Xaa Xaa Tyr Xaa Xaa Xaa Xaa Xaa Trp
1               5                   10

<210> SEQ ID NO 2
<211> LENGTH: 13
<212> TYPE: PRT
<213> ORGANISM: Homo sapiens
<220> FEATURE:
<221> NAME/KEY: misc_feature
<222> LOCATION: (10)..(10)
<223> OTHER INFORMATION: Xaa is proline or hydroxyproline

<400> SEQUENCE: 2

Tyr Glu Tyr Leu Asp Tyr Asp Phe Leu Xaa Glu Trp Glu
1               5                   10

<210> SEQ ID NO 3
<211> LENGTH: 14
<212> TYPE: PRT
<213> ORGANISM: Homo sapiens
<220> FEATURE:
<221> NAME/KEY: misc_feature
<222> LOCATION: (10)..(10)
<223> OTHER INFORMATION: Xaa is proline or hydroxyproline

<400> SEQUENCE: 3

Tyr Glu Tyr Leu Asp Tyr Asp Phe Leu Xaa Glu Trp Glu Pro
1               5                   10

<210> SEQ ID NO 4
<211> LENGTH: 15
```

```
<212> TYPE: PRT
<213> ORGANISM: Homo sapiens
<220> FEATURE:
<221> NAME/KEY: misc_feature
<222> LOCATION: (10)..(10)
<223> OTHER INFORMATION: Xaa is proline or hydroxyproline

<400> SEQUENCE: 4

Tyr Glu Tyr Leu Asp Tyr Asp Phe Leu Xaa Glu Trp Glu Pro Leu
1               5                   10                  15

<210> SEQ ID NO 5
<211> LENGTH: 13
<212> TYPE: PRT
<213> ORGANISM: Homo sapiens
<220> FEATURE:
<221> NAME/KEY: misc_feature
<222> LOCATION: (11)..(11)
<223> OTHER INFORMATION: Xaa is proline or hydroxyproline

<400> SEQUENCE: 5

Glu Tyr Glu Tyr Leu Asp Tyr Asp Phe Leu Xaa Glu Trp
1               5                   10

<210> SEQ ID NO 6
<211> LENGTH: 14
<212> TYPE: PRT
<213> ORGANISM: Homo sapiens
<220> FEATURE:
<221> NAME/KEY: misc_feature
<222> LOCATION: (11)..(11)
<223> OTHER INFORMATION: Xaa is proline or hydroxyproline

<400> SEQUENCE: 6

Glu Tyr Glu Tyr Leu Asp Tyr Asp Phe Leu Xaa Glu Trp Glu
1               5                   10

<210> SEQ ID NO 7
<211> LENGTH: 15
<212> TYPE: PRT
<213> ORGANISM: Homo sapiens
<220> FEATURE:
<221> NAME/KEY: misc_feature
<222> LOCATION: (11)..(11)
<223> OTHER INFORMATION: Xaa is proline or hydroxyproline

<400> SEQUENCE: 7

Glu Tyr Glu Tyr Leu Asp Tyr Asp Phe Leu Xaa Glu Trp Glu Pro
1               5                   10                  15

<210> SEQ ID NO 8
<211> LENGTH: 16
<212> TYPE: PRT
<213> ORGANISM: Homo sapiens
<220> FEATURE:
<221> NAME/KEY: misc_feature
<222> LOCATION: (11)..(11)
<223> OTHER INFORMATION: Xaa is proline or hydroxyproline

<400> SEQUENCE: 8

Glu Tyr Glu Tyr Leu Asp Tyr Asp Phe Leu Xaa Glu Trp Glu Pro Leu
1               5                   10                  15

<210> SEQ ID NO 9
<211> LENGTH: 14
<212> TYPE: PRT
<213> ORGANISM: Homo sapiens
<220> FEATURE:
<221> NAME/KEY: misc_feature
```

```
<222> LOCATION: (12)..(12)
<223> OTHER INFORMATION: Xaa is proline or hydroxyproline

<400> SEQUENCE: 9

Lys Glu Tyr Glu Tyr Leu Asp Tyr Asp Phe Leu Xaa Glu Trp
1               5                   10

<210> SEQ ID NO 10
<211> LENGTH: 15
<212> TYPE: PRT
<213> ORGANISM: Homo sapiens
<220> FEATURE:
<221> NAME/KEY: misc_feature
<222> LOCATION: (12)..(12)
<223> OTHER INFORMATION: Xaa is proline or hydroxyproline

<400> SEQUENCE: 10

Lys Glu Tyr Glu Tyr Leu Asp Tyr Asp Phe Leu Xaa Glu Trp Glu
1               5                   10                  15

<210> SEQ ID NO 11
<211> LENGTH: 16
<212> TYPE: PRT
<213> ORGANISM: Homo sapiens
<220> FEATURE:
<221> NAME/KEY: misc_feature
<222> LOCATION: (12)..(12)
<223> OTHER INFORMATION: Xaa is proline or hydroxyproline

<400> SEQUENCE: 11

Lys Glu Tyr Glu Tyr Leu Asp Tyr Asp Phe Leu Xaa Glu Trp Glu Pro
1               5                   10                  15

<210> SEQ ID NO 12
<211> LENGTH: 17
<212> TYPE: PRT
<213> ORGANISM: Homo sapiens
<220> FEATURE:
<221> NAME/KEY: misc_feature
<222> LOCATION: (12)..(12)
<223> OTHER INFORMATION: Xaa is proline or hydroxyproline

<400> SEQUENCE: 12

Lys Glu Tyr Glu Tyr Leu Asp Tyr Asp Phe Leu Xaa Glu Trp Glu Pro
1               5                   10                  15
Leu
```

SELECTIN INHIBITORS, COMPOSITION, AND USES RELATED THERETO

STATEMENT REGARDING FEDERALLY FUNDED RESEARCH

This invention was made with government support under Grants DK069275, HL106018, HL60963, and HL085607 awarded by the National Institutes of Health. The government has certain rights in the invention.

CROSS REFERENCE TO RELATED APPLICATIONS

This Application is the National Stage of International Application Number PCT/US2014/039308 filed May 23, 2014, which claims priority to U.S. Provisional Application No. 61/830,285 filed Jun. 3, 2013. The entirety of each of these applications is hereby incorporated by reference for all purposes.

INCORPORATION-BY-REFERENCE OF MATERIAL SUBMITTED AS A TEXT FILE VIA THE OFFICE ELECTRONIC FILING SYSTEM (EFS-WEB)

The Sequence Listing associated with this application is provided in text format in lieu of a paper copy, and is hereby incorporated by reference into the specification. The name of the text file containing the Sequence Listing is 13089US_ST25.txt. The text file is 4 KB, was created on Dec. 3, 2015, and is being submitted electronically via EFS-Web.

BACKGROUND

The selectin family of cell adhesion molecules, together with their glycoconjugate ligands, participate in leukocyte trafficking to sites of inflammation and to lymphoid organs. P- and E-selectins are expressed on activated vascular endothelial cells where they mediate initial tethering and rolling of leukocytes on endothelial cells by binding to P-selectin glycopeptide ligand-1 (PSGL-1) present on the surface of leukocytes. P-selectin is also expressed on activated platelets. L-selectin is expressed on the surface of leukocytes and mediates leukocyte-leukocyte interactions by binding to PSGL-1 present on the surface of other leukocytes promoting leukocyte accumulation to the inflammatory sites. Selectins recognize the sialyl Lewis x epitope (SLex, NeuAcα2-3Galβ1-4(Fucα1-3)GlcNAcβ1-) on glycoconjugate ligands. However, selectin binding to SLex determinant alone is low affinity and is necessary but not sufficient for physiological interactions. Thus, selectins require additional post-translational modifications or peptide components for high-affinity binding to their ligands. P- and L-selectin both bind to the extreme N-terminus of PSGL-1 and interact with three clustered tyrosine sulfate residues and a nearby core-2-based O-glycan with sialyl Lewis x epitope (C2—SLex). The N-terminus of human PSGL-1 contains three potential tyrosine sulfation sites (Y46, Y48 and Y51) and two potential O-glycan attachment sites (T44 and T57).

Leppanen et al. report that binding of glycosulfopeptides to P-selectin implicates stereospecific contributions of individual tyrosine sulfate and sugar residues. J Biol Chem., 2000, 275(50):39569-39578. Leppanen et al. also report that human L-selectin preferentially binds synthetic glycosulfopeptides modeled after endoglycan. Glycobiology, 2010, 20(9):1170-1185. See also WO 2003/032925, WO 99/65712, US 2002/0026033, U.S. Pat. No. 5,858,994, U.S. Pat. No. 6,136,790, Hicks et al. FASEB J, 2002, 16(11): 1461-1462, and Hicks et al. FASEB J, 2002, 16(5):A1052.

Ohta et al. report inhibition of P-selectin specific cell adhesion by a low molecular weight, non-carbohydrate compound, KF38789. Inflamm Res, 2001, 50(11):544-51.

Several small molecule inhibitors and protein therapeutics aimed at blocking PSGL-1/P-selectin interactions are already in clinical trials. Certain candidates pose production, stability, and immunity issues. Thus, there is a need for molecules that bind to selectins with high specificity and affinity, which in turn inhibit selectin mediated cell-cell interactions that have desirable pharmacological properties.

References cited herein are not an admission of prior art.

SUMMARY

This disclosure relates to selectin inhibitors, compositions, and methods related thereto. In certain embodiments, the disclosure relates to glycopeptides that contain one or more modified amino acids conjugated to a saccharide or polysaccharide. In certain embodiments, the disclosure relates to uses of the glycopeptides as anti-inflammatory, antithrombotic, or anti-metastatic agents.

In certain embodiments, the disclosure relates to isolated non-naturally occurring glycopeptides comprising $Y^1X^1Y^2X^2X^3Y^3X^4X^5X^6Z^1X^7W^1$ (SEQ ID NO: 1) or salts thereof, wherein $W^1$ is threonine or serine substituted with a saccharide or polysaccharide, $X^1$, $X^2$, $X^3$, $X^4$, $X^5$, $X^6$, and $X^7$ individually and independently any amino acid, $Y^1$, $Y^2$, and $Y^3$ are each individually and independently tyrosine, phenylalanine, or phenylglycine unsubstituted or substituted with —$SO_3H$, —$CH_2SO_3H$, —$CF_2SO_3H$, —$CO_2H$, —$CONH_2$, —$NHSO_2CH_3$, —$SO_2NH_2$, or —$CH_2PO_3H$, and $Z^1$ is proline or hydroxyproline.

In certain embodiment, the disclosure relates to pharmaceutical compositions comprising a glycopeptides disclosed herein and a pharmaceutically acceptable excipient. In certain embodiments, the pharmaceutical formulation is in the form of a pill, tablet, capsule, or gel or in the form of an aqueous saline buffer wherein the pharmaceutically acceptable excipient is a saccharide or polysaccharide.

In certain embodiments, this disclosure relates to methods of treating or preventing vascular disease or conditions such as atherosclerosis, atherosclerotic lesions, thrombus formation, thromboembolism, stroke, or myocardial infarction by administering an effective amount of a pharmaceutical composition disclosed herein to a subject in need thereof. In certain embodiments, the subject is at risk of, exhibiting symptoms of, or diagnosed with atherosclerosis, atherosclerotic lesions, thrombus formation, thromboembolism, stroke, or myocardial infarction.

In certain embodiments, the disclosure contemplates methods of treating or preventing allergies or lung diseases or conditions comprising administering an effective amount of a pharmaceutical composition disclosed herein to a subject in need thereof. In certain embodiments, the subject is at risk of, exhibiting symptoms of, or diagnosed with asthma, bronchitis, emphysema, and COPD.

In certain embodiments, the disclosure relates to methods of treating or preventing cancer or tumor metastasis comprising administering an effective amount of a pharmaceutical composition disclosed herein to a subject in need thereof.

In certain embodiments, the disclosure relates to the production of a medicament comprising glycosulfopeptides disclosed herein for uses disclosed herein.

In certain embodiments, the disclosure relates to methods of producing polysaccharides and glycopeptides disclosed herein comprising mixing starting materials and reagents under conditions such that the products are formed.

DETAILED DESCRIPTION

Figure 1:
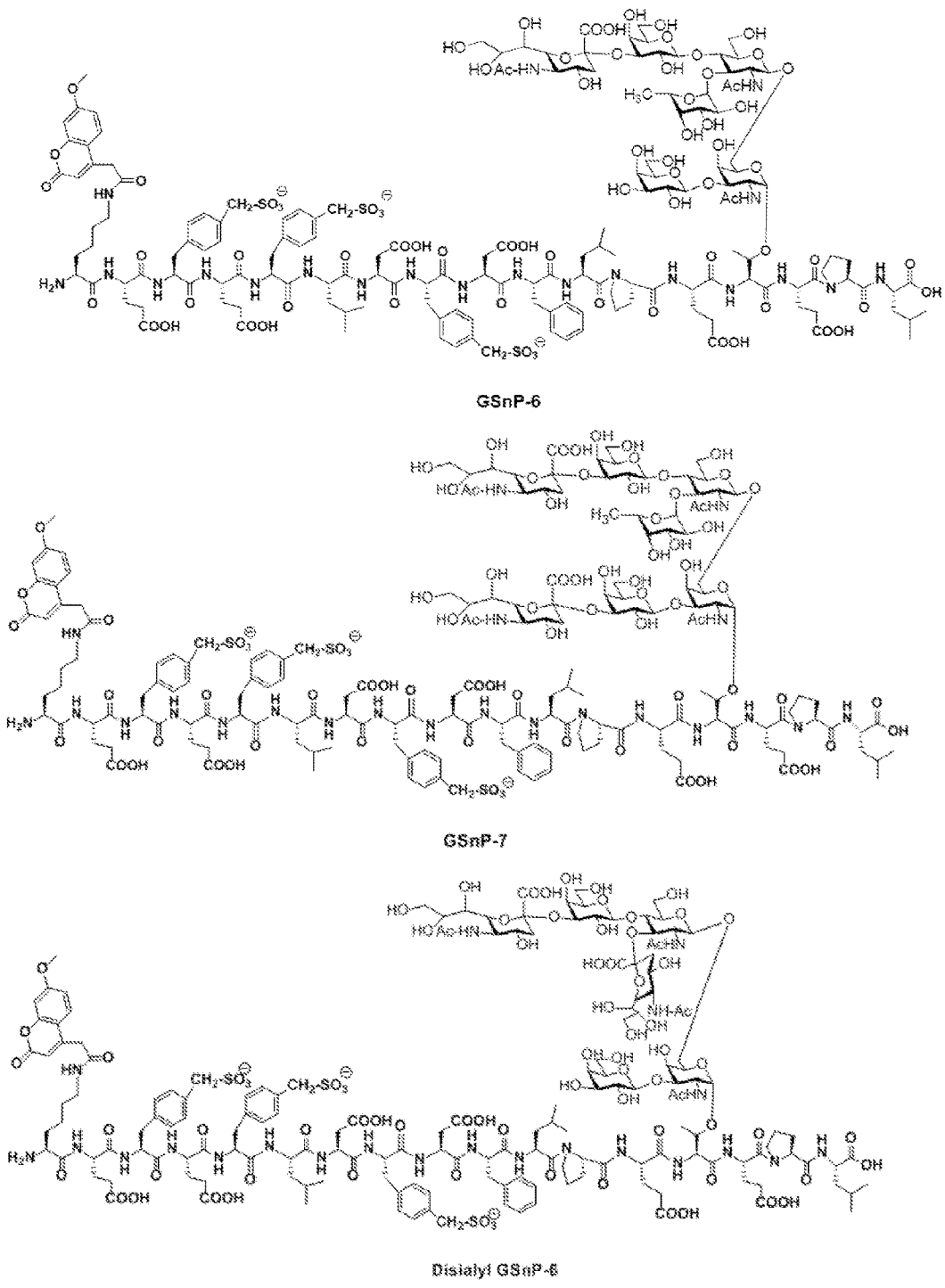
FIG. 1 illustrates certain glycosulfopeptides mimetics of PSGL-1.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, organic chemistry, biochemistry, molecular biology, pharmacology, physiology, and the like, which are within the skill of the art. Such techniques are explained fully in the literature.

It must be noted that, as used in the specification and the appended claims, the singular forms "a," "an," and "the" include plural referents unless the context clearly dictates otherwise. In this specification and in the claims that follow, reference will be made to a number of terms that shall be defined to have the following meanings unless a contrary intention is apparent.

Prior to describing the various embodiments, the following definitions are provided and should be used unless otherwise indicated.

As used herein, "salts" refer to derivatives of the disclosed compounds where the parent compound is modified making acid or base salts thereof. Examples of salts include, but are not limited to, mineral or organic acid salts of basic residues such as amines, alkylamines, or dialkylamines; alkali or organic salts of acidic residues such as carboxylic acids e.g., sodium or potassium salts of sulfonic acid, and the like. In typical embodiments, the salts are conventional nontoxic pharmaceutically acceptable salts including the quaternary ammonium salts of the parent compound formed, and nontoxic inorganic or organic acids. Preferred salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

"Subject" refers any animal, preferably a human patient, livestock, rodent, monkey or domestic pet.

As used herein, the terms "prevent" and "preventing" include the prevention of the recurrence, spread or onset. It is not intended that the present disclosure be limited to complete prevention. In some embodiments, the onset is delayed, or the severity of the disease is reduced.

As used herein, the terms "treat" and "treating" are not limited to the case where the subject (e.g., patient) is cured and the disease is eradicated. Rather, embodiments, of the present disclosure also contemplate treatment that merely reduces symptoms, and/or delays disease progression.

As used herein, the term "combination with" when used to describe administration with an additional treatment means that the agent may be administered prior to, together with, or after the additional treatment, or a combination thereof.

A "protecting group" refers to those moieties that are introduced into a molecule by chemical modification of a functional group in order to obtain chemoselectivity in a subsequent chemical reaction or to facilitate purification. Protecting groups may be categorized by the reaction conditions and/or reagents that are used to remove them such as acid labile protecting groups, base labile protecting groups and hydrogenation removable protecting groups. For example, acid labile protecting groups, such as tBu or Boc, typically decompose when exposed to strong acidic conditions providing a hydrogen substituent in place of tBu or Boc protecting group. Acetyl esters and thioesters of alcohols and thiols are examples of base labile protecting groups. Additional examples of protecting groups include, but are not limited to, 4-methoxy-2,3,6-trimethylphenyl)sulfonyl (Mtr), 2,2,5,7,8-pentamethyl-chroman-6-sulphonyl (Pmc), tosyl (Tos), mesitylenesulfonyl (Mts), 4,4'-dimethoxybenzhydryl (Mbh), 2,4,6-trimethoxybenzyl (Tmob), tripheylmethyl (Trt), 9-fluorenylmethyloxycarbonyl (fmoc), tert-butyl (tBu), benzyl (Bzl), t-butoxymethyl ether (Bum), (2,4-dinitrophenol) Dnp, benzyloxymethyl (Bom), benzyloxycarbonyl (Z), 2-chloro-benzyloxycarbonyl (CIZ), t-butyloxycarbonyl (Boc), formyl (CHO) or 2-bromobenzyloxycarbonyl (BrZ) and heterocycles such as succinimide, maleimide, and phathalimide. Protecting groups may be in the form of derivatives, e.g., having one or more substituents.

As used herein, the term "derivative" refers to a structurally similar compound that retains sufficient functional attributes of the identified analogue. The derivative may be structurally similar because it is lacking one or more atoms, substituted, a salt, in different hydration/oxidation states, or because one or more atoms within the molecule are switched, such as, but not limited to, replacing an oxygen atom with a sulfur or nitrogen atom or replacing an amino group with a hydroxyl group or vice versa. The derivative may be a prodrug. Derivatives may be prepare by any variety of synthetic methods or appropriate adaptations presented in synthetic or organic chemistry text books, such as those provide in March's Advanced Organic Chemistry: Reactions, Mechanisms, and Structure, Wiley, 6th Edition (2007) Michael B. Smith or Domino Reactions in Organic Synthesis, Wiley (2006) Lutz F. Tietze hereby incorporated by reference.

The term "substituted" refers to a molecule wherein at least one hydrogen atom is replaced with a substituent. When substituted, one or more of the groups are "substituents." The molecule may be multiply substituted. In the case of an oxo substituent ("=O"), two hydrogen atoms are replaced. Example substituents within this context may include halogen, hydroxy, alkyl, alkoxy, nitro, cyano, oxo, carbocyclyl, carbocycloalkyl, heterocarbocyclyl, heterocarbocycloalkyl, aryl, arylalkyl, heteroaryl, heteroarylalkyl, —$NR_aR_b$, —$NR_aC(=O)R_b$, —$NR_aC(=O)NR_aNR_b$, —$NR_aC(=O)OR_b$, —$NR_aSO_2R_b$, —$C(=O)R_a$, —$C(=O)OR_a$, —$C(=O)NR_aR_b$, —$OC(=O)NR_aR_b$, —$OR_a$, —$SR_a$, —$SOR_a$, —$S(=O)_2R_a$, —$OS(=O)_2R_a$ and —$S(=O)_2OR_a$. $R_a$ and $R_b$ in this context may be the same or different and independently hydrogen, halogen hydroxyl, alkyl, alkoxy, alkyl, amino, alkylamino, dialkylamino, carbocyclyl, carbocycloalkyl, heterocarbocyclyl, heterocarbocycloalkyl, aryl, arylalkyl, heteroaryl, heteroarylalkyl.

Substituted glycosulfopeptides Derivatives

A tyrosine derivative, 4-sulfonomethyl phenylalanine, chemical name 2-amino-3-(4-(sulfonomethyl)phenyl)propanoic acid, was incorporated into glycosulfopeptides as illustrated in FIG. 1. A chemoenzymatic synthetic scheme was developed for the generation of selectin ligand glycosulfopeptides. The amino acid Phe (p-$CH_2SO_3H$) may be prepared according to the procedures in Roosenburg et al., Bioconjugate Chem, 2010, 21, 663-670. Fmoc-Phe(4-$CH_2$—$SO_3H$) and other amino acids, such as Fmoc-Phg(4-$CH_2$—$SO_3Na$), Fmoc-Phe(4-$NO_2$), Fmoc-Phe(4-COO-tBu), Fmoc-Phe(4-C(O)$NH_2$), Fmoc-Phe(4-NH—$SO_2$—$CH_3$), and Boc-L-Phe[4-$CH_2$—$PO_3(bn)_2$]-OMe, are commercially available from RSP amino acids LLC, Shirley, Mass.

Certain embodiments were identified with nanomolar binding affinity to P-selectin. Blockade of P-selectin/PSGL-1 interactions inhibit leukocyte recruitment during inflammation. Certain substituted glycosulfopeptides derivatives modeled after N-terminus PSG1-1 sequence are P-selectin antagonist that are uniquely stable during chemical synthesis, and they are suitable for preparative scale synthesis. PSGL-1 normally contains tyrosine sulfate moieties which are typically unstable during chemical synthesis. Since sulfonate isosters are resistant to both hydrolysis and oxidation, the replacement of the tyrosine sulfate (X=$OSO_3$) moiety with a robust isosteric C-sulfonate (X=$CH_2SO_3$) overcomes the stability problem and affords compounds with high levels of P-selectin affinity. In the sulfonate analog (X=$SO_3$), although missing the oxygen atom linking the $SO_3$ and phenyl group, it retains the aromatic and anionic properties of tyrosine sulfate, and thus serves as a stable mimetic.

In certain embodiments, the disclosure relates to isolated glycopeptides comprising $Y^1X^1Y^2X^2X^3Y^3X^4X^5X^6Z^1X^7W^1$ (SEQ ID NO: 1) or salts thereof, wherein $W^1$ is threonine or serine substituted with a saccharide or polysaccharide, $X^1$, $X^2$, $X^3$, $X^4$, $X^5$, $X^6$, and $X^7$ individually and independently any amino acid, $Y^1$, $Y^2$, and $Y^3$ are each individually and independently tyrosine, phenylalanine, or phenylglycine unsubstituted or substituted with —$SO_3H$, —$CH_2SO_3H$, —$CO_2H$, —$CONH_2$, —$NHSO_2CH_3$, or —$CH_2PO_3H$, and $Z^1$ is proline or hydroxyproline.

In certain embodiments, at least one or two of $Y^1$, $Y^2$, and $Y^3$ are phenylalanine 4-substituted with sulfonomethyl.

In certain embodiments, all $Y^1$, $Y^2$, and $Y^3$ are phenylalanine 4-substituted with sulfonomethyl.

In certain embodiments, the polysaccharide is sialyl Lewis X or sialyl Lewis A. In certain embodiments, the polysaccharide comprises, 2-(acetylamino)-2-deoxy-galactose alpha 1 bonded to $W^1$,
galactose beta 3 bonded to 2-(acetylamino)-2-deoxy-galactose, 2-(acetylamino)-2-deoxy-glucose beta 6 bonded to 2-(acetylamino)-2-deoxy-galactose and Fucose is alpha 3 bonded to 2-(acetylamino)-2-deoxy-glucose.

In certain embodiments, the polysaccharide comprises,
2-(acetylamino)-2-deoxy-galactose alpha 1 bonded to $W^1$,
galactose beta 3 bonded to 2-(acetylamino)-2-deoxy-galactose,
2-(acetylamino)-2-deoxy-glucose beta 6 bonded to 2-(acetylamino)-2-deoxy-galactose,
fucose is alpha 3 bonded to 2-(acetylamino)-2-deoxy-glucose, and
galactose beta 4 bonded to 2-(acetylamino)-2-deoxy-glucose.

In certain embodiments, the polysaccharide comprises,
2-(acetylamino)-2-deoxy-galactose alpha 1 bonded to $W^1$,
galactose beta 3 bonded to 2-(acetylamino)-2-deoxy-galactose,
2-(acetylamino)-2-deoxy-glucose beta 6 bonded to 2-(acetylamino)-2-deoxy-galactose,
fucose is alpha 3 bonded to 2-(acetylamino)-2-deoxy-glucose,
galactose beta 4 bonded to 2-(acetylamino)-2-deoxy-glucose,
5-acetamido-3,5-dideoxy-glycero-galacto-2-nonulosonic acid alpha 3 bonded to galactose.

In certain embodiments, the polysaccharide comprises,
2-(acetylamino)-2-deoxy-galactose alpha 1 bonded to $W^1$,
galactose beta 3 bonded to 2-(acetylamino)-2-deoxy-galactose,
2-(acetylamino)-2-deoxy-glucose beta 6 bonded to 2-(acetylamino)-2-deoxy-galactose,
galactose beta 4 bonded to 2-(acetylamino)-2-deoxy-glucose,
5-acetamido-3,5-dideoxy-glycero-galacto-2-nonulosonic acid alpha 3 bonded to galactose, and
fucose is alpha 3 bonded to 2-(acetylamino)-2-deoxy-glucose.

In certain embodiments, the polysaccharide comprises,
2-(acetylamino)-2-deoxy-galactose alpha 1 bonded to $W^1$,
a first galactose beta 3 bonded to 2-(acetylamino)-2-deoxy-galactose,
2-(acetylamino)-2-deoxy-glucose beta 6 bonded to 2-(acetylamino)-2-deoxy-galactose,
a second galactose beta 4 bonded to 2-(acetylamino)-2-deoxy-glucose,
5-acetamido-3,5-dideoxy-glycero-galacto-2-nonulosonic acid is alpha 3 bonded to the second galactose,
fucose is alpha 3 bonded to 2-(acetylamino)-2-deoxy-glucose, and
5-acetamido-3,5-dideoxy-glycero-galacto-2-nonulosonic acid is alpha 3 bonded to the first galactose.

In certain embodiments, $X^1$, $X^3$, $X^4$, and $X^7$ is each individually and independently E, D, N, or Q.

In certain embodiments, $X^2$, $X^5$, and $X^6$ is each individually and independently L, I, V, A or F.

In certain embodiments, in certain embodiments, the disclosure relates to isolated glycopeptides comprising or consisting of $Y^1EY^2LDY^3DFLZ^1EW^1E$, (SEQ ID NO: 2)

$Y^1EY^2LDY^3DFLZ^1EW^1EP$, (SEQ ID NO: 3)

$Y^1EY^2LDY^3DFLZ^1EW^1EPL$, (SEQ ID NO: 4)

$EY^1EY^2LDY^3DFLZ^1EW^1$, (SEQ ID NO: 5)

$EY^1EY^2LDY^3DFLZ^1EW^1E$, (SEQ ID NO: 6)

$EY^1EY^2LDY^3DFLZ^1EW^1EP$, (SEQ ID NO: 7)

$EY^1EY^2LDY^3DFLZ^1EW^1EPL$, (SEQ ID NO: 8)

$KEY^1EY^2LDY^3DFLZ^1EW^1$, (SEQ ID NO: 9)

$KEY^1EY^2LDY^3DFLZ^1EW^1E$, (SEQ ID NO: 10)

$KEY^1EY^2LDY^3DFLZ^1EW^1EP$, (SEQ ID NO: 11)
or $KEY^1EY^2LDY^3DFLZ^1EW^1EPL$. (SEQ ID NO: 12)

In certain embodiments, the disclosure relates to an isolated glycopeptides comprising $KEY^1EY^2LDY^3DFLZ^1EW^1EPL$ (SEQ ID NO: 12) or salt thereof wherein, $W^1$ is threonine, $Y^1$, $Y^2$, and $Y^3$ are phenylalanine 4-substituted with sulfonomethyl, $Z^1$ is proline;

2-(acetylamino)-2-deoxy-galactose alpha 1 bonded to $W^1$,
galactose beta 3 bonded to 2-(acetylamino)-2-deoxy-galactose,
2-(acetylamino)-2-deoxy-glucose beta 6 bonded to 2-(acetylamino)-2-deoxy-galactose,
fucose is alpha 3 bonded to 2-(acetylamino)-2-deoxy-glucose,
galactose beta 4 bonded to 2-(acetylamino)-2-deoxy-glucose, and
5-acetamido-3,5-dideoxy-glycero-galacto-2-nonulosonic acid is alpha 3 bonded to galactose.

In certain embodiments, the disclosure relates to compositions comprising intermediate compounds such as of the following formula,

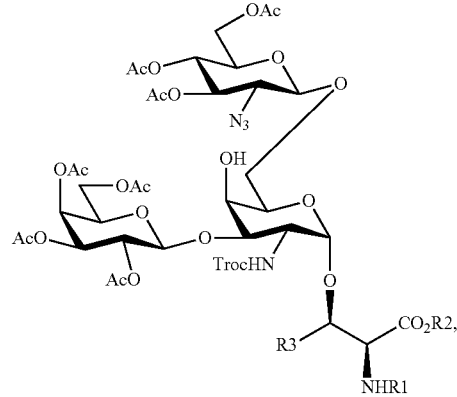

wherein R1 is hydrogen, a protecting group, an amino protecting group, or a base removable protecting group and R2 is hydrogen, a protecting group, a carboxylic acid protecting group or a acid removable protecting group or wherein R1 is hydrogen, a carboxylic acid protecting group or a acid removable protecting group and R2 is hydrogen, amino protecting group or a base removable protecting group and R3 is hydrogen, an amino acid side chain, or alkyl optionally substituted with one or more substituent.

In certain embodiments, the base removable protecting group is the heterocyclic base removable protecting group Fmoc.

In certain embodiments, the acid removable protecting group is tert-butyl or Boc.

Pharmaceutical Compositions

In certain embodiment, the disclosure relates to pharmaceutical compositions comprising a glycopeptides disclosed herein and a pharmaceutically acceptable excipient. In certain embodiments, the pharmaceutical formulation is in the form of a pill, tablet, capsule, or gel or in the form of an aqueous saline buffer wherein the pharmaceutically acceptable excipient is a saccharide or polysaccharide.

As used herein the language "pharmaceutically acceptable excipient" is intended to include any and all carriers, solvents, diluents, excipients, adjuvants, dispersion media, coatings, antibacterial and antifungal agents, and absorption delaying agents, and the like, compatible with pharmaceutical administration.

Suitably, the pharmaceutical composition of the disclosure comprises a carrier and/or diluent appropriate for its delivering by injection to a human or animal organism. Such carrier and/or diluent is non-toxic at the dosage and concentration employed. It is selected from those usually employed to formulate compositions for parental administration in either unit dosage or multi-dose form or for direct infusion by continuous or periodic infusion. It is typically isotonic, hypotonic or weakly hypertonic and has a relatively low ionic strength, such as provided by sugars, polyalcohols and isotonic saline solutions. Representative examples include sterile water, physiological saline (e.g. sodium chloride), bacteriostatic water, Ringer's solution, glucose or saccharose solutions, Hank's solution, and other aqueous physiologically balanced salt solutions (see for example the most current edition of Remington: The Science and Practice of Pharmacy, A. Gennaro, Lippincott, Williams & Wilkins). The pH of the composition of the disclosure is suitably adjusted and buffered in order to be appropriate for use in humans or animals, typically at a physiological or slightly basic pH (between about pH 8 to about pH 9, with a special preference for pH 8.5). Suitable buffers include phosphate buffer (e.g. PBS), bicarbonate buffer and/or Tris buffer. A typical composition is formulated in 1M saccharose, 150 mM NaCl, 1 mM MgCl2, 54 mg/l Tween 80, 10 mM Tris pH 8.5. Another typical composition is formulated in 10 mg/ml mannitol, 1 mg/ml HSA, 20 mM Tris, pH 7.2, and 150 mM NaCl.

The composition of the disclosure can be in various forms, e.g. in solid (e.g. powder, lyophilized form), or liquid (e.g. aqueous). In the case of solid compositions, the typical methods of preparation are vacuum drying and freeze-drying which yields a powder of the active agent plus any additional desired ingredient from a previously sterile-filtered solution thereof. Such solutions can, if desired, be stored in a sterile ampoule ready for reconstitution by the addition of sterile water for ready injection.

Nebulized or aerosolized formulations also form part of this disclosure. Methods of intranasal administration include the administration of a droplet, spray, or dry powdered form of the composition into the nasopharynx of the individual to be treated from a pressured container or dispenser which contains a suitable propellant, e.g., a gas such as carbon dioxide, or a nebulizer (see for example WO 95/11664). Enteric formulations such as gastroresistant capsules and granules for oral administration, suppositories for rectal or vaginal administration also form part of this disclosure. For non-parental administration, the compositions can also include absorption enhancers which increase the pore size of the mucosal membrane. Such absorption enhancers include sodium deoxycholate, sodium glycocholate, dimethyl-beta-cyclodextrin, lauroyl-1-lysophosphatidylcholine and other substances having structural similarities to the phospholipid domains of the mucosal membrane.

The composition can also contain other pharmaceutically acceptable excipients for providing desirable pharmaceutical or pharmacodynamic properties, including for example modifying or maintaining the pH, osmolarity, viscosity, clarity, color, sterility, stability, rate of dissolution of the formulation, modifying or maintaining release or absorption into an the human or animal organism. For example, polymers such as polyethylene glycol may be used to obtain desirable properties of solubility, stability, half-life and other pharmaceutically advantageous properties (Davis et al., 1978, Enzyme Eng. 4, 169-173; Burnham et al., 1994, Am. J. Hosp. Pharm. 51, 210-218). Representative examples of stabilizing components include polysorbate 80, L-arginine, polyvinylpyrrolidone, trehalose, and combinations thereof. Viscosity enhancing agents include sodium carboxymethylcellulose, sorbitol, and dextran. The composition can also contain substances known in the art to promote penetration or transport across the blood barrier or membrane of a particular organ (e.g. antibody to transferrin receptor; Friden et al., 1993, Science 259, 373-377). A gel complex of poly-lysine and lactose (Midoux et al., 1993, Nucleic Acid Res. 21, 871-878) or poloxamer 407 (Pastore, 1994, Circulation 90, 1-517) can be used to facilitate administration in arterial cells.

The composition may be administered to patients in an amount effective, especially to enhance an immune response in an animal or human organism. As used herein, the term "effective amount" refers to an amount sufficient to realize a desired biological effect. The appropriate dosage may vary depending upon known factors such as the pharmacodynamic characteristics of the particular active agent, age, health, and weight of the host organism; the condition(s) to be treated, nature and extent of symptoms, kind of concurrent treatment, frequency of treatment, the need for prevention or therapy and/or the effect desired. The dosage will also be calculated dependent upon the particular route of administration selected. Further refinement of the calculations necessary to determine the appropriate dosage for treatment is routinely made by a practitioner, in the light of the relevant circumstances. The titer may be determined by conventional techniques. The administration may take place in a single dose or a dose repeated one or several times after a certain time interval.

Methods of Use

P-selectin plays an important role during the initial steps of leukocyte recruitment to the sites of inflammation. Thus, the development of therapeutics that block P-selectin/PSGL-1 interactions is desirable. Substituted tyrosine glycosulfopeptides derivatives such as GSnP-6 could be useful for treating atherosclerosis, inflammatory bowel disease, sickle cell disease, ischemia and reperfusion injury, coagulopathies, lung diseases, tumor metastasis, as well as having diagnostic applications.

Selectins promote tumor metastasis. See Laubli & Borsig, Semin Cancer Biol, 2010, 20(3):169-77. Gong et al. report P-selectin-mediated platelet activation promotes adhesion of non-small cell lung carcinoma cells on vascular endothelial cells. Mol Med Rep, 2012, 5(4):935-42. Cui et al. report differential expression of the alpha 2,3-sialic acid residues in breast cancer is associated with metastatic potential. Oncol Rep, 2011, 25(5):1365-71. See also Shirure et al., PLoS One. 2012, 7(9):e44529 and Pérez-Garay et al., PLoS One, 2010, 5(9):e12524.

In certain embodiments, the disclosure relates to methods of treating or preventing cancer or tumor metastasis comprising administering an effective amount of a pharmaceutical composition disclosed herein to a subject in need thereof.

In certain embodiments, the disclosure relates to methods of treating or preventing cancer comprising administering an effective amount of a compound disclosed herein to a subject in need thereof. In certain embodiments, the subject diagnosed with, exhibiting symptoms of, or at risk of cancer. In certain embodiments, the cancer is venous ulcers, angiogenic disorders of the skin, a hematological malignancy, a leukemia, lymphoma, acute lymphoblastic leukemia (ALL), acute myelogenous leukemia (AML), chronic lymphocytic leukemia (CLL), small lymphocytic lymphoma (SLL), chronic myelogenous leukemia, acute monocytic leukemia (AMOL), Hodgkin's lymphomas, non-Hodgkin's lymphomas, Burkitt lymphoma, B-cell lymphoma, multiple myelomacervical, ovarian cancer, colon cancer, breast cancer, gastric cancer, lung cancer, melanoma, skin cancer, ovarian cancer, pancreatic cancer, prostate cancer, head cancer, neck cancer, and renal cancer.

In certain embodiments, cancer therapeutic strategies entail pharmaceutical compositions comprising a glycopeptide disclosed herein administered in combination with a second anti-cancer agent such as gefitinib, erlotinib, docetaxel, cis-platin, 5-fluorouracil, gemcitabine, tegafur, raltitrexed, methotrexate, cytosine arabinoside, hydroxyurea, adriamycin, bleomycin, doxorubicin, daunomycin, epirubicin, idarubicin, mitomycin-C, dactinomycin and mithramycin, vincristine, vinblastine, vindesine, vinorelbine taxol, taxotere, etoposide, teniposide, amsacrine, topotecan, camptothecin, bortezomib, anagrelide, tamoxifen, toremifene, raloxifene, droloxifene, iodoxyfene, fulvestrant, bicalutamide, flutamide, nilutamide, cyproterone, goserelin, leuprorelin, buserelin, megestrol, anastrozole, letrozole, vorazole, exemestane, finasteride, marimastat, trastuzumab, cetuximab, dasatinib, imatinib, bevacizumab, combretastatin, thalidomide, and/or lenalidomide or combinations thereof.

Certain selectins activate cell adhesion to the vascular endothelium allowing them to infiltrate tissue from the circulating blood. P-, E-, and L-selectin mediate migration of activated CD8+ T lymphocytes into inflamed skin. Hirata et al., J Immunol, 2002, 169:4307-13. Culmer et al. report that circulating and vein wall P-selectin promote venous thrombogenesis during aging in a rodent model and assert that this is evidence supporting the use of selectin targeted therapeutics for the prophylaxis and treatment of venous thrombosis. Thrombosis Research, 2012, 131:42-48. Westmuckett & Moore report a lack of tyrosylprotein sulfotransferase activity in hematopoietic cells drastically attenuates atherosclerosis. Arterioscler Thromb Vasc Biol, 2009, 29:1730-1736.

In certain embodiments, the disclosure relates to methods of treating or preventing a vascular disease or condition comprising administering an effective amount of a pharmaceutical composition disclosed herein to a subject in need thereof.

In certain embodiments, the subject is a human that is at risk of, exhibiting symptoms of, or diagnosed with atherosclerosis, peripheral vascular disease, coronary heart disease, heart failure, right ventricular hypertrophy, cardiac dysrhythmia, endocarditis, inflammatory cardiomegaly, myocarditis, vascular heart disease, stroke, cerebrovascular disease, or peripheral arterial disease.

In certain embodiments, this disclosure relates to methods of treating or preventing vascular disease or conditions such as atherosclerosis, atherosclerotic lesions, thrombus formation, thromboembolism, stroke, or myocardial infarction by administering an effective amount of a pharmaceutical composition disclosed herein to a subject in need thereof. In certain embodiments, the subject is at risk of, exhibiting symptoms of, or diagnosed with atherosclerosis, atherosclerotic lesions, thrombus formation, thromboembolism, stroke, or myocardial infarction.

In certain embodiments, the subject has type I or type II diabetes, impaired glucose tolerance, elevated serum C-reactive protein concentration, vitamin B6 deficiency, dietary iodine deficiency, hypothyroidism, hyperlipidemia, hypertension, or is older than 50 years old, or smokes cigarettes daily.

In certain embodiments, the pharmaceutical composition is administered in combination with a statin, atorvastatin, cerivastatin, fluvastatin, lovastatin, mevastatin, pitavastatin, pravastatin, rosuvastatin, simvastatin, ezetimibe, amlodipine, niacin, aspirin, omega-3 fatty acid, or combinations thereof.

Selectin antagonists are also useful for the treatment of lung diseases such as asthma, bronchitis, emphysema, and COPD. Bimosiamose is a pan-selectin antagonist that attenuates late asthmatic reactions following allergen challenge and attenuates airway inflammation in COPD. See Beeh et al., Pulm Pharmacol Ther, 2005, 19:233-4 and Watz et al., Pulmonary Pharmacology & Therapeutics 26 (2013) 265-270. Schumacher et al. report that P-selectin glycopeptide ligand-1 (PSGL-1) is up-regulated on leukocytes from patients with chronic obstructive pulmonary disease. Clin Exp Immunol, 2005, 142:370-6.

In certain embodiments, the disclosure contemplates methods of treating or preventing allergies or lung diseases or conditions comprising administering an effective amount of a pharmaceutical composition disclosed herein to a subject in need thereof. In certain embodiments, the subject is at risk of, exhibiting symptoms of, or diagnosed with asthma, bronchitis, emphysema, and COPD.

In certain embodiments, this disclosure related to using compound disclosed herein for the treatment or prevention of inflammatory disorders. In certain embodiments, the disclosure relates to the treatment or prevention of inflammation or an inflammatory disorder comprising administering a compound disclosed herein to a subject in need thereof. In certain embodiments, the inflammation is a result of cardiac ischemia, injury, or a pathogenic infection, e.g. viral, bacterial, fungal, or the inflammatory disorder is selected from atherosclerosis, allergies, acne vulgaris, asthma, autoimmune diseases, celiac disease, prostatitis, glomerulonephritis, hypersensitivities, inflammatory bowel disease, pelvic inflammatory disease, arthritis, rheumatoid arthritis, sarcoidosis, transplant rejection, vasculitis, or interstitial cystitis.

In certain embodiments, the disclosure relates to treating inflammation or an inflammatory disease or condition by administering an effective amount of a compound disclosed herein in combination with an anti-inflammatory agent such as salicylates, aspirin (acetylsalicylic acid), diflunisal, salsalate, propionic acid derivatives, ibuprofen, dexibuprofen, naproxen, fenoprofen, ketoprofen, dexketoprofen, flurbiprofen, oxaprozin, loxoprofen, acetic acid derivatives, indomethacin, tolmetin, sulindac, etodolac, ketorolac, diclofenac, nabumetone, enolic acid (oxicam) derivatives, piroxicam, meloxicam, tenoxicam, droxicam, lornoxicam, isoxicam, fenamic acid derivatives (fenamates), mefenamic acid, meclofenamic acid, flufenamic acid, tolfenamic acid, selective COX-2 inhibitors (voxibs), celecoxib, rofecoxib, valdecoxib, parecoxib, lumiracoxib, etoricoxib, firocoxib, sulphonanilides, nimesulide, licofelone, and combinations thereof.

EXPERIMENTAL

Compound Synthesis

Krishnamurthy et al. report the synthesis of an Fmoc-threonine bearing core-2 glycan as a building block for PSGL-1 via Fmoc-assisted solid-phase peptide synthesis. *Carbohydr Res* 2010, 345(11): 1541-1547. However, this method suffered from suboptimal regioselectivity in the glycosylation step (2.6:1). Furthermore, the approach required a triflic azide mediated diazotransfer, which due to the explosive nature of neat $TfN_3$. To circumvent these problems, our approach was revised to provide a short, convenient route synthesis of glycoamino acid compound 7 with improved regioselectivity and yield (See FIG. 2).

The synthesis began from 3,4,6 tri-O-acetyl-D-galactal, which could be readily converted to a halide via a one pot azidochlorination step. Direct coupling of the chloride intermediate with a Fmoc-threonine acceptor was unsuccessful due to rapid decomposition. Therefore, this intermediate was converted in situ to the thioglycoside donor compound 1. Significantly, this two-step, one pot procedure could be carried out on a preparative scale (>50 gram) to provide donor compound 1 in 67% yield. Coupling of compound 1 to the Fmoc-threonine acceptor proceeded to compound 2 in 78% yield with very high a-selectivity. De-O-acetylation of compound 2 under Zemplen conditions, selective 4,6 acetal protection, and glycosylation with galactose donor compound 3 under NIS/TfOH conditions, afforded benzylidene protected compound 4 in 89% yield. Starting from 3,4,6 tri-O-acetyl-D-galactal, this diol compound 5 is obtained in 7 steps in 21% overall yield.

In the glycosylation step with acceptor compound 5, the axial 4-OH group was anticipated to be of low reactivity, especially when carrying a substituent at O-3. However, an undesired tetrasaccharide was identified in approximately 20% yield. Both desired and undesired compounds had similar retention factor values. Thus, chromatographic separation was challenging and laborious, particularly at a preparative scale. To address this problem, low temperature activation (−10° C.) was performed with glucosamine donor compound 6 at 0.8 Equiv (as opposed to 1.2 Equiv), which produced only the β-glycoside compound 7 in 79% yield. The (1→6)-linkage in compound 7 was confirmed by NOESY spectrum, which displayed a cross-peak between H-1 of the glucosamine residue and H-6 of the galactosamine residue. gHMBC NMR of compound 7 confirmed that O-6 was glycosylated in revealing cross-peaks from 101.3 ppm (C-1 of the glucosamine residue, A-C1) and 4.02 ppm (H-6 of the galactosamine residue, BH6), as well as from 4.70 ppm (H-1 of the glucosamine residue, A-H1) and 69.5 ppm (C-6 of the galactosamine residue, B-C6). Acetylation of compound 7 with $Py/Ac_2O$, zinc reduction, and TFA mediated tert-butyl ester deprotection provided the Core-2 O-glycan compound 9 and offered an alternative route to similar glycoamino acid building blocks for glycopeptide synthesis.

Figures 1, 2:
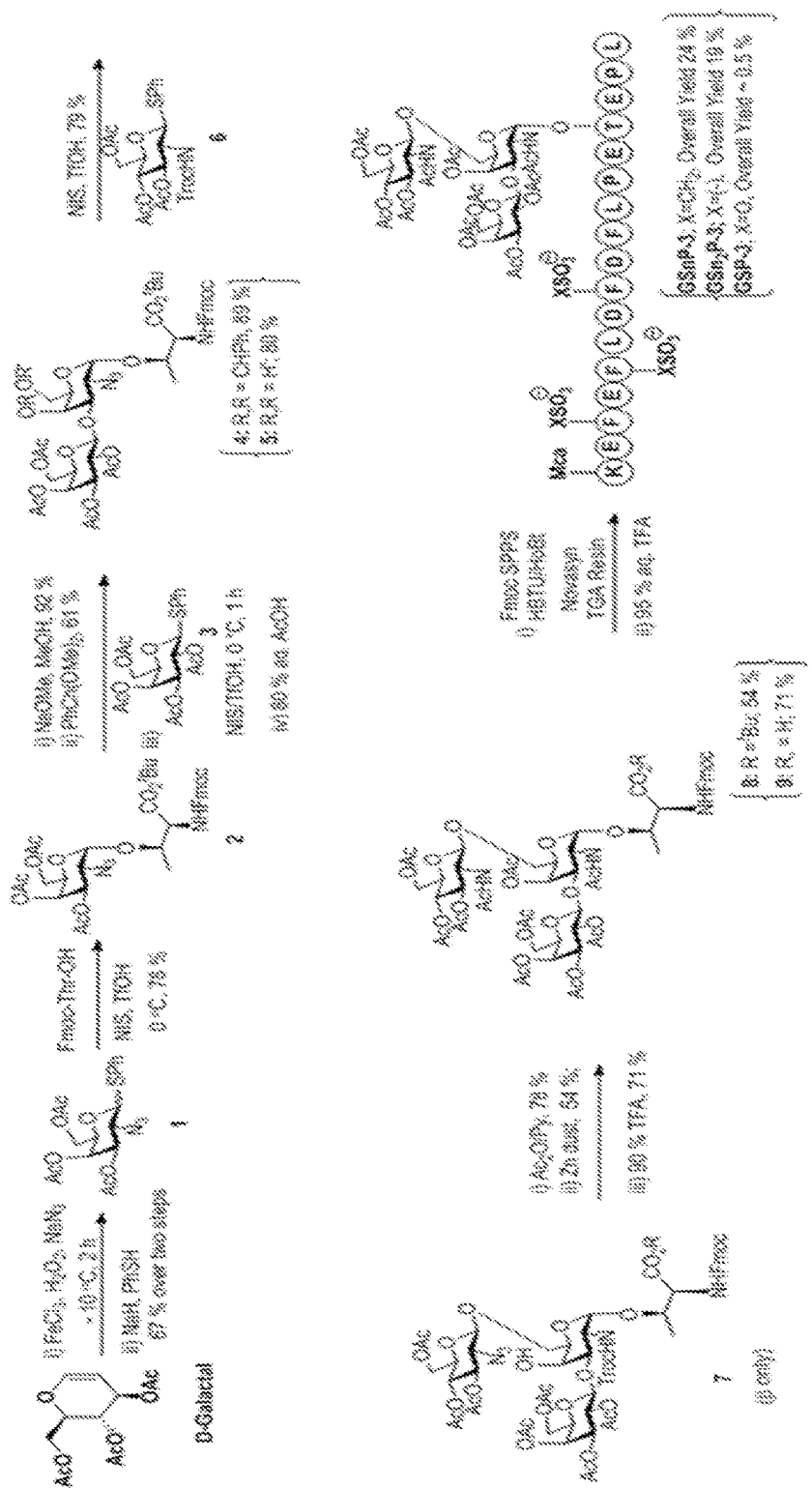
FIG. 2 illustrates the synthesis of the Core-2 glycan and subsequent enzymatic steps to afford a family of glycopeptide mimetics of PSGL-1. Enzymatic steps (a) UDP-Gal, β-1,4-GalT (bovine), alkaline phosphatase, 130 mM HEPES, pH 7.4, 40 mM sodium cacodylate, pH 7.0, 20 mM $MnCl_2$, and 0.02% NaN3; (b) α 2,3-(N)-sialylT CMP-NeuAc 50 mM MOPS, pH 7.4, 0.1% bovine serum albumin, and 0.02% NaN3, 14 h; (c) GDP-Fuc, α-1,3-FucT-VI, 50 mM MOPS, pH 7.4, 20 mM $MnCl_2$ and 0.02% NaN3, 16 h. Disialyl GSnP-6 was obtained from GSnP-4 in 45% yield. GSnP-7 was obtained in 55% yield by fucosylation of disialyl GSnP-6. 4-(Sulfomethyl) series (n): GSnP-6 (X: CH2; R=H); GSnP-7 (X: CH2; R=Sialyl); 4-(Sulfo)phenylalanine series (n2): GSn2P-6 (X: bond; R=H); Tyrosine O-sulfate series: GSP-6 (X: O; R=H). The last numeral refers to the size of the glycan (e.g. 6 for hexasaccharide).
Figure 2:
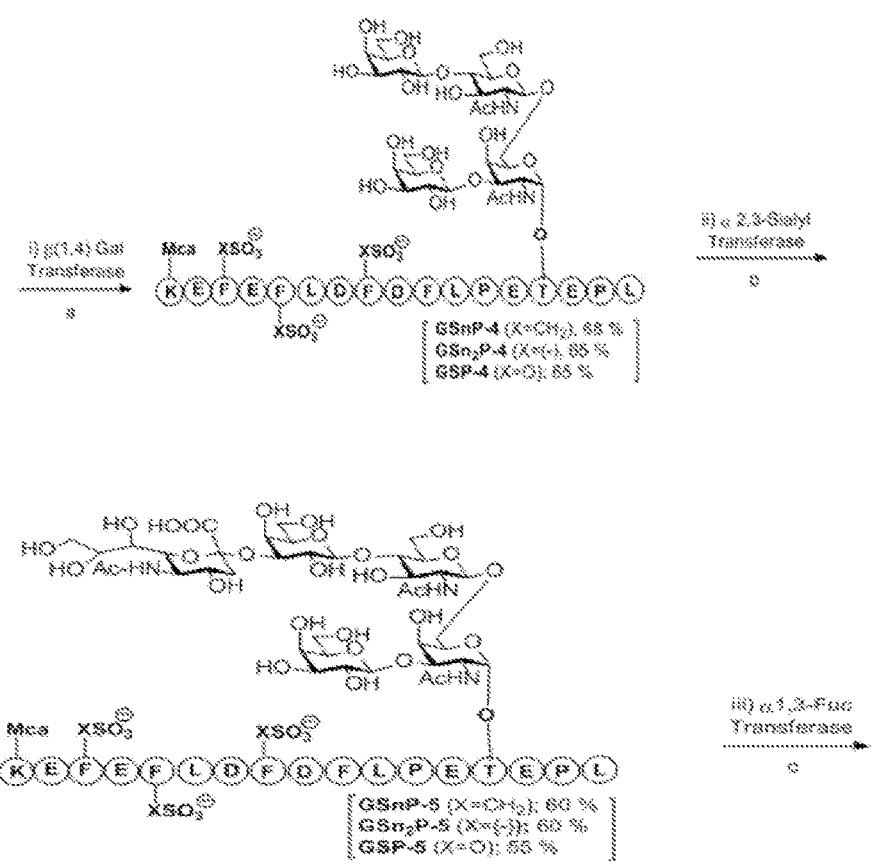

The glycopeptide binding site of PSGL-1 was synthesized using a Fmoc assited SPPS strategy (FIG. 2). Fmoc-Phe $(CH_2SO_3H)$—OH and Fmoc-Phe$(SO_3H)$—OH amino acids were purchased from RSP Amino Acids LLC. Coupling reactions were performed using 2-(1H-benzotriazole-1-yl)-1,1,3,3-tetramethyluronium hexafluorophosphate (HBTU) and 1-hydroxy-benzotriazol (HOBt). Fmoc groups were removed with 20% piperidine/dimethylformamide without affecting the O-acetyl groups or inducing β-elimination of the glycan. The presence of a N-fluorenyl (Fmoc) group allowed for photometric monitoring of the coupling reaction ($\lambda$=300.5 nm). For sulfonate mimics, Fmoc-Phe$(CH_2SO_3)$Na and Fmoc-Phe$(SO_3)$Na coupling reactions proceeded smoothly, while coupling with Fmoc-Tyr$(OSO_3)$Na amino acid was found to be difficult. The latter effect was presumably due to the electron withdrawing nature of tyrosine sulfates, which deactivated the peptide sequence and reduced coupling efficiency. Deprotection was carried out using TFA mediated conditions (95% TFA/2.5% TES/2.5% $H_2O$) at room temperature for 1 h. The O-acetate group was saponified using catalytic NaOMe in methanol to afford glycopeptide mimics $GS_{(n)}P$-3, which were further purified by RP-HPLC. When tyrosine O-sulfates were employed in peptide synthesis overall yield of GSP-3 was less than 0.5%. In contrast, the hydrolytically stable sulfonate analogues resulted in a dramatic improvement of the overall yield to afford GSnP-3 and $GSn_2P$-3 in 24% and 19% yields, respectively.

The sLe$^x$ moiety was constructed on $GS_{(n)}P$-3 by using glycosyltransferases in stepwise, sequential addition of galactose, sialic acid, and fucose. The highly efficient β1,4-galactosyltransferase (β1,4-GalT) is commercially available and was used to initially install β1,4-galactose. Since sialyltransferases have low efficiency towards a fucosylated Le$^x$ structure, fucose was installed after sialylation. Thus, galactose was first appended in a β1,4 linkage to GlcNAc by treatment with β1,4-GalT in the presence UDP-Galactose to produce GS(n)P-4. Similarly, addition of sialic acid was achieved by incubation of GsnP-4 with α2,3-sialyltransferase (α,2,3-(N)-sialylT) in the presence of CMP-NeuAc to obtain GSnP-5. The sLe$^x$ structure was completed by incubation of $GS_{(n)}P$-5 with human α1,3-fucosyltransferase V (1,3-FucT V) and GDP-Fucose to produce $GS_{(n)}P$-6. Enzymatic steps typically proceeded with 60 to 70% yield without observed interference of the sulfonate residues. In addition, desialylated glycopeptide mimics were generated through additional sialylation of GSnP-4 to provide disialyl GSnP-6 (45% yield) followed by fucosylation to provide GsnP-7 in 55% yield. By utilizing this approach, four sets of glycopeptides mimics of PSGL-1 were synthesized, including GSnP[3-6], disialyl GSnP-6, GSnP-7, $GSn_2P$[3-6], GSP [3-6], and three GSnP Core-1 peptides (FIG. 2).

Synthesis of Phenyl 3,4,6-tri-O-acetyl-2-azido-2-deoxy-1-thio-β-D-galactoside 1

3,4,6-Tri-O-acetyl-D-galactal (50 g, 0.2 mol) was dissolved in acetonitrile (700 mL). Ferric chloride hexahydrate (40 g, 0.15 mol, 0.8 eq.), sodium azide (13 g, 0.20 mol, 1.1 eq.) and hydrogen peroxide (21 mL, 0.20 mol, 1.1 eq.; 33% aq. solution) were added subsequently and the clear red-brown solution was stirred at −20° C. for 1 h. After 1 h, 5 mL of hydrogen peroxide solution was further added and stirred for additional 1 h at −10° C. The reaction mixture was diluted with dichloromethane (300 mL) and washed with water (4×70 mL), sat. NaHCO$_3$ (2×100 mL), and NaCl solution (2×100 mL) until the organic layer was colorless. $^1$H-NMR (500 MHz, CDCl3): # [ppm]=2.07 (s, 3 H), 2.08 (s, 3 H), 2.17 (s, 3 H), 4.09-4.13 (m, 2 H), 4.17 (dd, J=11.4, 3.4, 1 H), 4.52 (m, 1 H), 5.38 (dd, J=10.8, 3.2, 1 H), 5.51 (dd, J=3.1, 1.0, 1 H), 6.18 (d, J=3.3 Hz, 1 H); $^{13}$C-NMR (125.8 MHz, CDCl3): # [ppm]=20.6, 20.6, 20.7, 58.5, 60.9, 66.8, 68.7, 69.7, 92.6, 169.6, 169.9, 170.5. The crude chloride intermediate (55 g, 0.15 mol) was subsequently dissolved in dichlromethane (100 mL) and cooled to 0° C. To this solution was added sodium hydride (7.2 g, 0.18 mol, 60% dispersion in mineral oil) and thiophenol (20 mL, 018 mol). The reaction mixture was stirred at to 0° C. for 1 h and slowly warmed up to room temperature. After 12 h, The reaction mixture was diluted with dichlromethane (200 mL) and the mixture was filtered through celite. The organic phase was separated, dried, and concentrated under reduced pressure. Subsequent purification by chromatography over silica gel (Eluent: 40% ethyl acetate in hexane) thioglycoside donor 1 (α/β~1/1) as colorless oil (52 g, 67% yield). 1α-thioglycoside $^1$H NMR (CDCl$_3$, 600 MHz) 1α: δ 1.99 (s, 3H, OAc), 2.09 (s, 3H, OAc), 2.15 (s, 3H, OAc), 4.10 (2H, d, J 6.5 Hz, H-6), 4.33 (1H, dd, H-2), 4.78 (1H, t, H-5), 5.17 (1H, dd, J 11.1 Hz, H-3), ), 5.19 (1H, dd, J 11.1 Hz, H-3), 5.51 (d, 1H, J 3.3 Hz, H-4), 5.72 (d, 1H, J 5.5 Hz, H-1), d 7.30-7.55 (m, 5H, aromatic). 1β-thioglycoside $^1$H NMR (CDCl3): δ

δ 2.05 (s, 3H, OAc), 2.07 (s, 3H, OAc), 2.10 (s, 3H, OAc), 3.64 (1H, t, H-2), 3.91 (1H, t, H-5), 4.13 (1H, dd, J 6.3 Hz, H-6b), 4.19 (1H, dd, J 6.8 Hz, 11.3 Hz, H-6a), 4.50 (1H, d, J 10.1 Hz, H-1), 4.88 (1H, dd, J 10.3 Hz, H-3), ), 5.40 (1H, dJ 3.2 Hz, H-4), 7.32-7.65 (m, 5H, aromatic).

Synthesis of N$^α$-(Fluoren-9-ylmethoxycarbonyl)-O-{O-(2',3',4',6'-tetra-O-acetyl-β-D-galactopyranosyl)-(1→3)-O-[3",4",6"-tri-O-acetyl-2-deoxy-2-(2,2,2trichloroethoxycarbonylamino)-β-D-glucopyranosyl-(1→6)]-2-azido-2-deoxy-α-D-galactopyranosyl-L-threonine tent-butyl ester 7

Troc Glucosamine donor 6 (2.60 g, 4.8 mmol) and Core-1 acceptor 5 (2.80 g, 3.2 mmol) were mixed with freshly activated 4 Å molecular sieves (2 g). The reaction mixture was suspended in dichloromethane (50 mL) and cooled to –10° C. N-iodosuccinimide (1.8 g, 8.0 mmol) was slowly added over the period of 30 min with vigorous suspension of the reaction mixture. Trifluoromethanesulfonic acid (700 µL, 0.8 mmol) was added slowly and the stirring was continued at –10° C. for 2 h. The reaction mixture was filtered through celite into an aqueous solution of sodium thiosulfate with disappearance of the dark red color as the solution became colorless. The organic phase was separated, dried, and concentrated under reduced pressure. Subsequent purification by chromatography over silica gel (Eluent: 60% ethyl acetate in hexane) to afford only the desired trisaccharide 7 (3.1 g, 79% yield). Analytical data for 7: [α]$_D$+45.4 (c 1, CHCl$_3$); $^1$H NMR (CDCl$_3$, 600 MHz): δ 1.31 (3H, d, J 6.0 Hz, Thr —CH$_3$), 1.51 (9H, s, —NHBoc), 1.98 (3H, s, OAc), 2.00 (3H, s, OAc), 2.01 (3H, s, OAc), 2.02 (3H, s, OAc), 2.05 (3H, s, OAc), 2.08 (3H, s, OAc), 2.10 (3H, s, OAc), 3.54 (1H, d, J 10.8 Hz, Gal-N$_3$ H-2), 3.67 (1H, m), 3.74 (1H, m), 4.4-4.2 (12 H, m), 4.6-4.5 (2H, m, Fmoc CH), 4.67 (1H, d, J 8.4 Hz, Thr CH$^β$), 4.70 (1H, d, J 12.0 Hz, GlcNTroc-1,6 H-1), 4.74 (1H, d, J 7.8 Hz, Gal H-1), 4.83 (1H, d, J 12.6 Hz), 4.99 (1H, d, J 9.0 Hz, Gal N$_3$ H-1), 5.11 (3H, m), 5.26 (1H, ddd, J 8.4 Hz, 12 Hz, 22.5 Hz, Gal H-2), 5.28 (1H, d, J 3.0 Hz, GlcNTroc-1,6 H-3), 5.52 (1H, d, J 8.4 Hz), 5.61 (1H, d, J 9.6 Hz, Gal H-4), 6.07 (1H, d, J 9.6 Hz, Thr —NH), 7.16 (1H, d, J 6.6 Hz), 7.32 (2H, dd, J 7.2Hz, 7.8 Hz, -Fmoc Ar), 7.43 (2H, m, -Fmoc Ar), 7.63 (2H, d, J 7.2 Hz, -Fmoc Ar), 7.77 (2H, d, J 7.8 Hz, -Fmoc Ar); $^{13}$C NMR (150 MHz, CDCl$_3$): δ$_C$ 19.2, 20.7, 20.8, 20.9, 20.9, 28.2, 47.3, 56.5, 58.7, 59.2, 61.5, 62.2, 67.0, 67.7, 68.6, 68.7, 69.2, 69.3, 70.9, 71.3, 72.5, 72.1, 74.6, 75.6, 83.4, 95.6, 99.2, 101.3, 102.2, 120.2, 125.1, 125.3, 127.2, 127.3, 127.9, 141.5, 143.9, 144.0, 154.2, 157.1, 158.7, 159.3, 169.5, 169.7, 169.9, 170.3, 170.4, 170.6, 170.8, 170.9; HRESIMS Calcd for C$_{58}$H$_{72}$O$_{27}$N$_5$Cl$_3$ [M+K]$^+$ 1414.31144; found 1414.31119.

Synthesis of N$^α$-(Fluoren-9-ylmethoxycarbonyl)-O-{O-(2',3',4',6'-tetra-O-acetyl-β-D-galactopyranosyl)-(1→3)-O-[3",4",6"-tri-O-acetyl-2-deoxy-2-acetamido-β-D-glucopyranosyl-(1→6)]-2-acetamido-2-deoxy-4-O-acetyl-β-D-galactopyranosyl-L-threonine 9

The trisaccharide 9 was synthesized from 7 by the protocol in Krishnamurthy Carbohydr Res 2010, 345(11): 1541-1547Analytical Data for 9 [α]$_D$+35.7 (c 1, CHCl$_3$); $^1$H NMR (CDCl$_3$, 600 MHz): δ$_H$ 1.21 (3H, d, J 6.6 Hz, Thr —CH$_3$), 2.04 (30 H, s, 10×3 OAc's), 2.48 (1H, br. s, —OH), 3.43 (1H, t, J 8.4 Hz), 3.69-3.66 (2H, m), 3.83-3.79 (4H, m), 4.13-4.04 (5H, m), 4.29-4.22 (5H, m), 4.42 (1H, d, J 6.0 Hz), 4.56-4.51 (3H, m), 4.68 (1H, d, J 7.8 Hz), 4.84 (m, 1H), 4.92 (m, 1H), 5.03-4.97 (m, 2H), 5.25 (m, 2H), 5.32 (1H, d, J 3.6 Hz), 7.30 (2H, ddd, J 3.0 Hz, 7.8 Hz, 7.8 Hz, -Fmoc Ar), 7.39 (2H, ddd, J 4.2 Hz, 7.8 Hz, 7.8 Hz, -Fmoc Ar), 7.50 (1H, br. s —NH), 7.60 (2H, d, J 7.2 Hz, -Fmoc Ar), 7.76 (2H, d, J 6.6 Hz, -Fmoc Ar); $^{13}$C NMR (150 MHz, CDCl$_3$): δ$_C$ 18.5, 20.7, 20.8, 20.9, 22.9, 23.1, 29.8, 47.4, 49.3, 49.4, 49.5, 49.7, 49.8, 50.0, 54.8, 58.5, 61.1, 62.1, 66.7, 66.9, 68.5, 68.6, 68.7, 68.8, 69.5, 70.7, 70.9, 72.0, 72.5, 76.1, 98.9, 99.0, 100.5, 101.0, 120.1, 125.0, 127.3, 127.4, 127.9, 141.5, 143.9, 144.0, 157.0, 157.2, 169.7, 169.8, 170.6, 170.8, 171.0, 171.1, 172.1; HRESIMS Calcd for C$_{57}$H$_{71}$O$_{28}$N$_3$ [M+H]$^+$ 1246.1769 found 1246.4297.

Procedure for Solid Phase Synthesis of Glycopeptides (GS$_{(n)P}$-3's)

The glycopeptides (GS$_n$P-3's) were synthesized manually on a Novasyn TGA resin using standard Fmoc amino acid coupling strategy: Briefly, Fmoc-Leu-Novasyn TGA resin (5×4 µmol, 0.3 mmol/g) was loaded into a polypropylene centrifuge filter tube (0.22 µM micron, Corning International) equipped with a plastic cap. The resin in each polypropylene tube was swelled by stirring gently with 4×500 µL dichloromethane (DCM) for 10 min and filtered. The coupling reaction was performed with Fmoc-amino acids (24 µmol, 120 µL, 0.2 M), HBTU (24 µmol, 120 µL, 0.2 M), HOBt (24 µmol, 120 µL, 0.3 M), DIPEA (36 µmol, 120 µL, 0.3 M). The coupling steps were allowed for 2 h twice, except the sulfonate analogs whose coupling reaction was 10 h. Fmoc cleavage was performed with 20% piperidine in DMF (400 µL) for 10 min twice. Deprotection and side chain removal of glycopeptides was accomplished by gently stirring in 500 µL of TFA cocktail (95/2/2/1: TFA/H$_2$O/EDT/triethylsilane. (Note: For GS$_{(n)}$P-3 the cleavage step was performed at room temperature for 1 h. For GSP-3, the TFA cleavage step needed to be performed at 4° C. for 12 h as reported previously). After this, the solution was evaporated and glycopeptides could be precipitated by addition of 10 mL cold diethylether. Next, the glycopeptides was dissolved in methanol to which few drops of NaOMe was added, stirred for 1 h and subsequently purified by RP-HPLC (condition: water 75%-60%+0.1% TFA in 20 min for $GS_{(n)}P$-3 and water 80%-65%+100mM ammonium acetate in 20 minutes for GSP-3) and lyophilized to obtain $GS_{(n)}P$-3's as a white powder (GSnP-3 $R_t$=16.9 min; $GSn_2P$-3 $R_t$=15.1 min; GSP-3 $R_t$=20.1 min). In MALDI-TOF analysis for GSnP-3 the observed $[M-H_2O]^-$ m/z is 3223.462 (calculated $[M-H_2O]^-$ $C_{141}H_{192}N_{20}O_{60}S_3$ m/z 3223.3261). For $GSn_2P$-3 the observed $[M-H_2O]^-$ m/z is 3179.660 (calculated $[M-H_2O]^-$ $C_{138}H_{186}N_{20}O_{60}S_3$ m/z 3179.1280). For GSP-3, the observed $[M-3SO_3]^-$ for ammonium adduct is m/z 3021.742 (calculated $[M-3SO_3]^-$ $C_{138}H_{188}N_{21}O_{55}$ m/z 3021.0770).

Procedure for Synthesis of $GS_{(n)}P$-4

$GS_{(n)}P$-3 (0.4 mM) was galactosylated using 125 milliunits of bovine milk β1,4-GalT (Sigma) and UDP-Gal (1.5 mM) in a total volume of 9.5 ml of 40 mM sodium cacodylate, pH 7.0, 20 mM $MnCl_2$, and 0.02% $NaN_3$. After 20 h of incubation at 37° C., a sample from the reaction mixture was analyzed by RP-HPLC which showed that all GS(n)P-3 had been converted into a faster moving product to afford $GS_{(n)}P$-4 (GSnP-4 $R_t$=16.0 min; $GSn_2P$-4 $R_t$=14.9 min; GSP-4 $R_t$=19.5 min). Glycopeptide samples were deproteinated and desalted in a Sephadex G-50 column (10 ml, 0.7-3.25 cm) using water or 25 mM $NH_4HCO_3$ as an eluant. 0.5-ml fractions were collected, and the glycopeptides were detected by measuring UV absorbance at 254 nm. In MALDI-TOF analysis for GSnP-4 the observed $[M-10H]^-$ m/z is 3332.106 (calculated $[M-10H]^-$ $C_{145}H_{192}N_{20}O_{64}S_3$ m/z 3333.154): For $GSn_2P$-4. the observed $[M-10H]^-$ for potassium adduct is 3334.524 (calculated $C_{142}H_{187}N_{20}O_{64}S_3K$ m/z 3335.010): For GSP-4, the observed $[M-3SO_3]^{31}$ is m/z 3181.568 (calculated $[M-3SO_3]^-$ $C_{145}H_{198}N_{20}O_{60}$ m/z 3181.2216).

Procedure for Synthesis of $GS_{(n)}P$-5

$GS_{(n)}P$-4 (1 mM) was sialylated using 20 milliunits of α2,3-(N)-sialylT (Calbiochem, La Jolla, Calif.) and 3 mM CMP-NeuAc (Sigma) in a total volume of 6.0 ml of 50 mM MOPS, pH 7.4, 0.1% bovine serum albumin, and 0.02% $NaN_3$. After 14 h of incubation at 37° C., the sample was analyzed by RP-HPLC, which showed that GS(n)P-4 had been converted completely into a faster moving product, GS(n)P-5 (GSnP-5 $R_t$=15.8 min; $GSn_2P$-5 $R_t$=14.3 min; GSP-5 $R_t$=19.1 min). In MALDI-TOF analysis for GSnP-5 the observed $[M-NH_3]^-$ m/z is 3621.655 (calculated $C_{156}H_{218}N_{20}O_{72}S_3$ m/z 3621.685): For $GSn_2P$-5. the observed $[M-10H]^-$ for potassium adduct is 3625.112 (calculated $C_{153}H_{204}N_{21}O_{72}S_3K$ $[M-10H]^-$ m/z 3624.647). For GSP-5, the observed $[M-3SO_3]^-$ is m/z 3471.994 (calculated $[M-3SO_3]^-$ $C_{156}H_{215}N_{21}O_{68}$ m/z 3472.4762). Disialylation of GSnP-4 provided Disialyl-GSnP-6 compound in 45% yield: In MALDI-TOF analysis for Disialyl-GSnP-6 the observed $[M-10H]^-$ m/z is 3915.048 (calculated $[M-10H]^-$ $C_{167}H_{226}N_{22}O_{80}S_3$ m/z 3915.345).

Procedure for Synthesis of $GS_{(n)}P$-6

3-FucT-VI-GS(n)P-5 (0.4 mM) was α1,3-fucosylated for 16 h at 37° C. with 2 milliunits of α1,3-Fucosyltransferase-VI (Calbiochem) and GDP-Fucose (0.8 mM) (Calbiochem) in a total volume of 3.5 ml of 50 mM MOPS, pH 7.4, 20 mM $MnCl_2$ and 0.02% $NaN_3$. Deproteinated and desalted sample was analyzed by RP-HPLC, which showed that GS(n)P-5 was converted completely into the product $GS_{(n)}P$-6 (GSnP-6 $R_t$=15.5 min; $GSn_2P$-6 $R_t$=14.1 min; GSP-6 $R_t$=19.0 min). Starting with 12 mg of GSnP-3, the overall recovery of GSnP-6 was 5.5 mg, as determined by UV absorbance at 275 nm during the HPLC runs. In MALDI-TOF analysis for GSnP-6 the observed $[M-NH_3]^-$ m/z is 3766.923 (calculated $[M-NH_3]^-$ $C_{162}H_{227}N_{20}O_{76}S_3$ m/z 3766.819): In ESI-QTOF analysis for GSnP-6 the observed triply charged species $[M-H]^{3-}$ m/z is 1259.7906 (calculated $[M-H]^{3-}$ $C_{162}H_{228}N_{21}O_{76}S_3$ m/z 1259.7927); Observed doubly charged species $[M-H]^{2-}$ m/z is 1890.1857 (calculated $[M-2H]^{2-}$ $C_{162}H_{228}N_{21}O_{76}S_3$ m/z 1890.916): In MALDI-TOF analysis for $GSn_2P$-6, the observed $[M-CO_2]^-$ is 3769.587 (calculated $C_{161}H_{229}N_{21}O_{76}S_3$ $[M-CO_2]^-$ m/z 3768.38621). For GSP-6, the observed $[M-3SO_3]^-$ is m/z 3615.470 (calculated $[M-3CO_3]^-$ $C_{162}H_{225}N_{21}O_{72}$ m/z 3615.4590). Fucosylation of Disialyl-GSnP-6 compound afforded GSnP-7 in 55% yield. In MALDI-TOF analysis for GSnP-7 the observed m/z $[M-10H]^-$ 4061.042 (calculated $[M-10H]^-$ $C_{173}H_{236}N_{22}O_{84}S_3$ m/z 4061.40338.

GSnP-6 Demonstrates Nanomolar Affinity to P-selectin

Binding affinities of PSGL-1 mimics towards selectins was initially screened using a microarray in which glycosulfopeptides and glycan standards (Sialyl Le$^x$, NA2, NA2, 3, NA2,6 and LNnT) were printed on a NHS-activated glass slide. The slide was then incubated with recombinant Ig chimeras of P-, L-, or E-selectin (5-20 μg/mL) followed by Alexa-488 labeled anti-human IgG antibody (5 μg/mL). Similar to a native PSGL-1 sequence containing tyrosine sulfate (GSP-6), GSnP-6 bound to P-selectin more strongly than to E- or L-selectin. Likewise, GSnP-7, a sialylated extension of GSnP-6, showed higher affinity to P-selectin. However, disialyl GSnP-6, lacking the fucosyl residue displayed lower affinity to P-selectin consistent with the key contribution of α-1,3-fucose. Binding of glycopeptides mimics to selectins was $Ca^{2-}$ dependent and inhibited by EDTA.

Dissociation constants ($K_d$) were determined using a Biacore binding assay after initial capture of biotinylated $GS_{(n)}P$-6 onto streptavidin-coated sensor chips followed by flow through of P-, L- or E-sel-Ig (2.5 to 60 μg/mL). Dissociation constants for GSnP-6 and $GSn_2P$-6 to human P-selectin were 22 nM and 14 nM, respectively; compared to the $K_d$ of 73 nM for native PSGL-1. The $K_d$ of GSnP-6 to murine P-selectin was ~9-fold lower than to human P-selectin. GSnP-6 bound to E- and L-selectin with even lower apparent affinity.

Figures 2, 3:
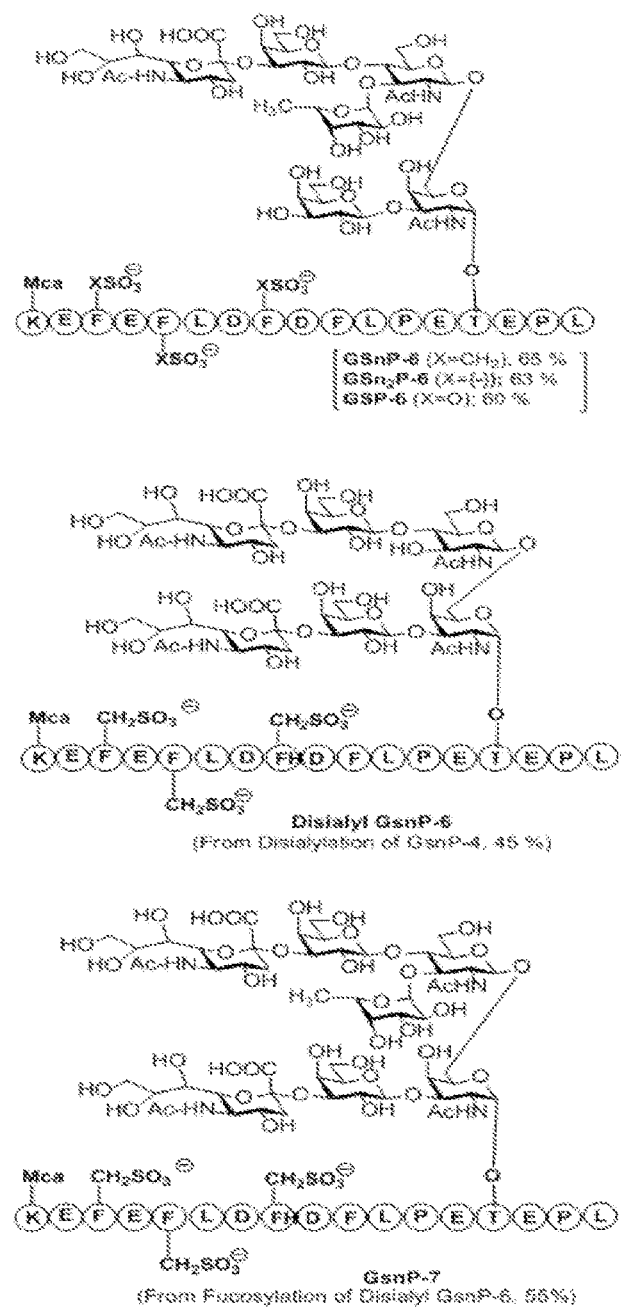
FIG. 3 shows data on microarray binding screen of glycopeptide mimics to (A) human and mouse P-selectin (5 μg/mL), (B) human and mouse L-selectin (20 μg/mL), and (C) human and mouse E-selectin (20 μg/mL) Reference compounds included Sialyl Lewis x ($SLe^x$), the biantennary glycans NA2, NA2,3, NA2,6, mannotriose-di-(N-acetyl-D-glucosamine), as well as lacto-N-neo-tetraose (LNnT) and biotin. Bound peptides were detected using Alexa-488 labeled anti-human IgG antibody (5 μg/mL). Three lectins RCA-1, AAL, and PNA were used to confirm the sequence of enzymatic steps. Monoclonal antibodies CHO131, PSG2 antibody and PL-1 were used to confirm the presence of SLex, tyrosine sulfates, and the peptide sequence, respectively. Biacore binding analysis to human P-selectin with observed rate constants for (D) GSnP-6, $k_{on}$ $3.1 \times 10^5$ $M^{-1}s^{-1}$, $k_{off}$ $6.9 \times 10^3$ $M^{-1}s^{-1}$; $GSn_2P$-6, $k_{on}$ $6.4 \times 10^5$ $M^{-1}s^{-1}$, $k_{off}$ $6.8 \times 10^3$ $M^{-1}s$. Biacore binding analysis to mouse P-selectin with observed rate constants for (E) GSnP-6, $k_{on}$ $4.9 \times 10^4$ $M^{-1}s^{-1}$, $k_{off}$ $8.0 \times 10^3$ $M^{-1}s$; $GSn_2P$-6 $k_{on}$ $5.3 \times 10^4$ $M^{-1}s^{-1}$, $k_{off}$ $9.0 \times 10^3$ $M^{-1}s$. (F) Temperature- and pH-dependent stability studies of GSnP-6.
Figures 1, 3:
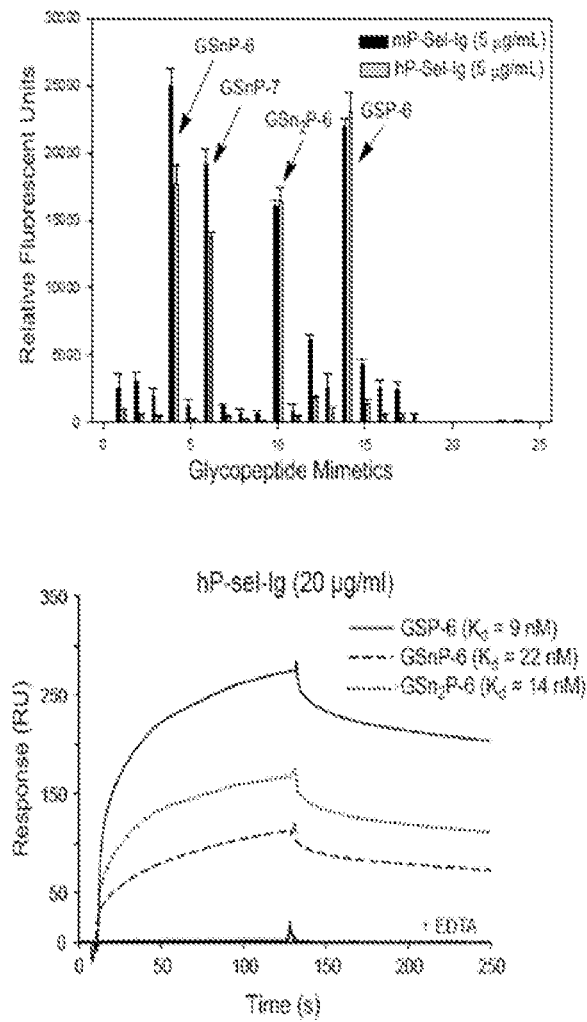
Figures 2, 3:
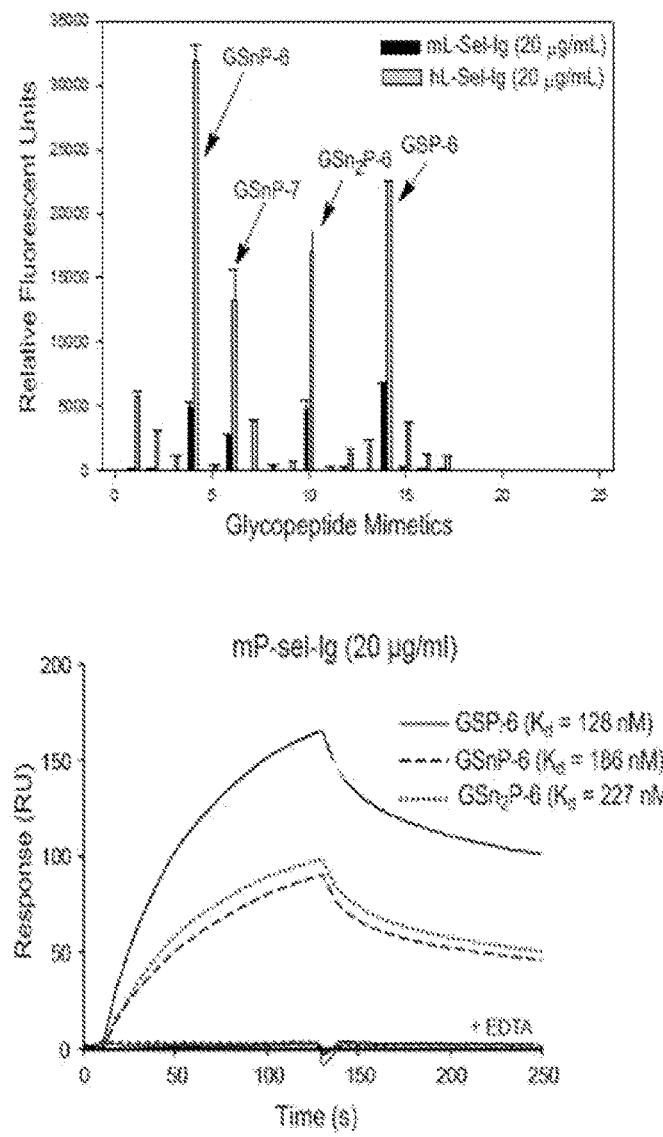
Figure 3:
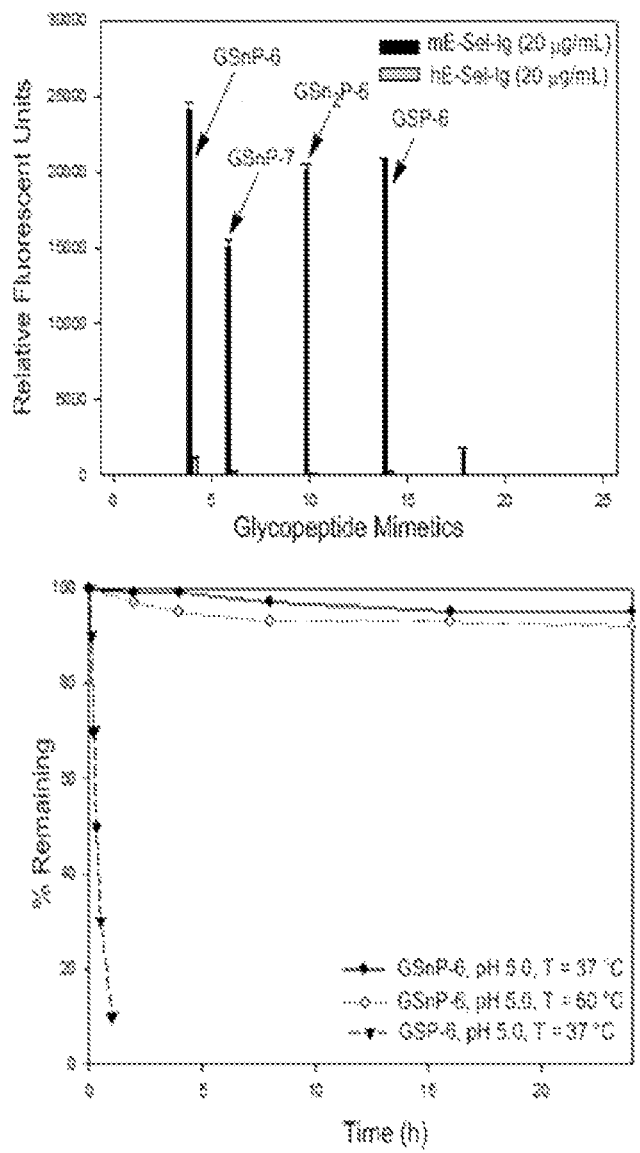
Figure 4:
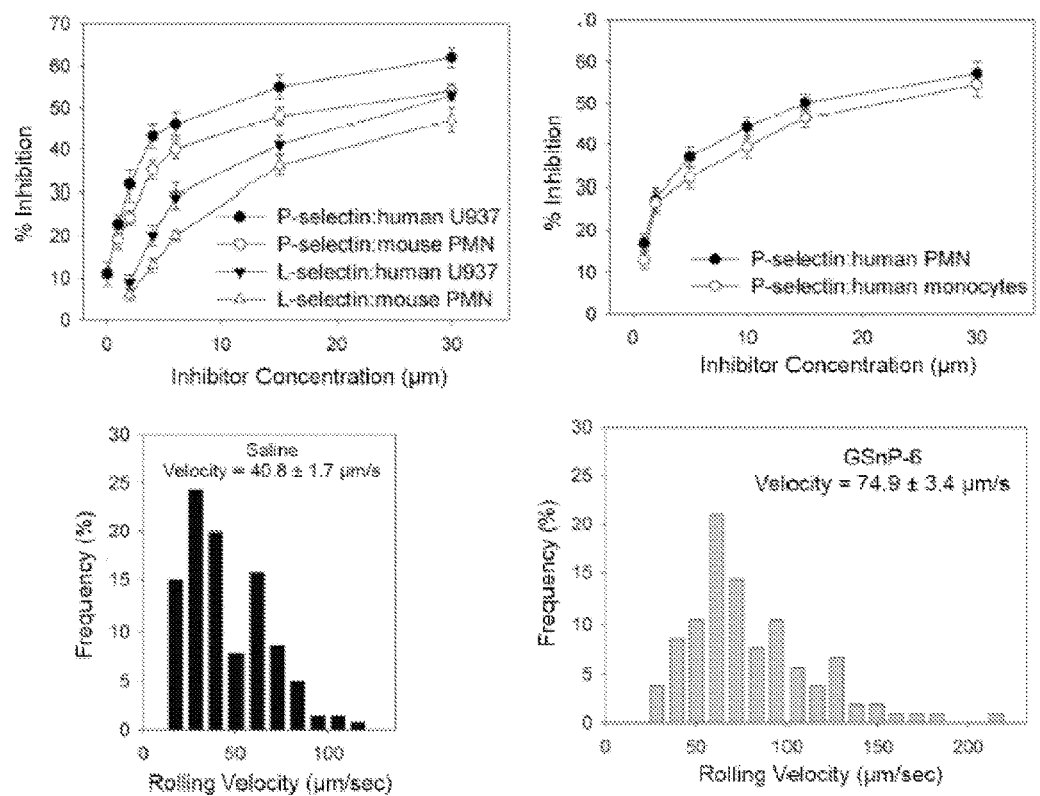
FIG. 4 shows data on (A) Florescence activated cell sorting (FACS) performed to determine the capacity of GSnP-6 to inhibit P and L-selectin binding to murine and U937 leukocytes, as well as to (B) human peripheral blood monocytes and neutrophils. (C) Intravital microscopy of the murine cremaster muscle microcirculation demonstrated increased leukocyte rolling velocity after intravenous administration of GSnP-6 (4 μmol/kg IV; p≤0.01).

The chemical stability of GSnP-6 was evaluated under low pH conditions by incubating the compound in sodium acetate/acetic acid buffer at pH 5, 37° C., as well as under high temperature conditions by incubation in 2 mM phosphate buffer at pH 7.5, 60° C. (FIG. 3E). The native N-terminal PSGL-1 sequence, GSP-6 rapidly degrades under these conditions, whereas degraded products were not detected for GSnP-6 by RP-HPLC.

GSnP-6 Inhibits P-selectin/PSGL-1 Dependent Interactions in Vitro.

Flow cytometry was used to characterize the ability of GSnP-6 to block binding of selectin-IgG chimeras to murine and human leukocytes. Recombinant mouse P- or L-selectin Fc chimera (2 μg/mL) was incubated with murine neutrophils and GSnP-6 (0-30 μM). Likewise, recombinant human P-selectin or L-selectin Fc chimera were incubated with human peripheral blood neutrophils and monocytes, as well as the human U937 cell line in the presence of GSnP-6 (0-30 μM). Binding of selectin-IgG chimeras was detected with PE-conjugated anti-IgG antibody, quantified as mean fluorescent intensity, and plotted as percent inhibition. Specificity was confirmed with selectin-specific blocking antibodies. GSnP-6 inhibited P-selectin dependent interactions in a dose dependent manner in all four cell lines, including human U-937 cells ($IC_{50}$~8 μM), murine PMN ($IC_{50}$~15 μM), human monocytes ($IC_{50}$~30 μM), human PMN ($IC_{50}$~30 μM). GSnP-6 also inhibited PSGL-1/L-selectin interactions, as assessed with human U-937 cells ($IC_{50}$~30 μM) and murine neutrophils ($IC_{50}$>50 μM).

GSnP-6 Inhibits Leukocyte Rolling in Vivo

Intravital microscopy was used to determine the ability of GsnP-6 to inhibit leukocyte binding to microvascular endothelium. PSGL-1 expressed on circulating leukocytes binds to selectins on endothelium; inducing leukocyte rolling to facilitate subsequent tight binding to integrin receptors. Inhibition of this interaction leads to an increase in rolling velocity. Intravital microscopy of the murine cremaster muscle microcirculation was performed on venules with a diameter of 30 to 40 μm. Seven venules per mouse (n=4, saline (control); n=3, GSnP-6, 4 μmol/kg IV) were analyzed and the velocities of 5 to 10 rolling leukocytes were determined in each venule by individually tracking leukocyte distance/time (μm/s). A significant increase in mean rolling velocity was observed after intravenous administration of GSnP-6 (FIG. GsnP-6: 74.9±3.4 μm/s, saline: 40.8±1.7 μm/s; p≤0.01).

What we claim:

1. A glycopeptide comprising $Y^1X^1Y^2X^2Y^3X^3Y^3X^4X^5X^6Z^1X^7W^1$ (SEQ ID NO: 1) or salts thereof, wherein $W^1$ is threonine or serine substituted with a saccharide or polysaccharide, $X^1$, $X^2$, $X^3$, $X^4$, $X^5$, $X^6$, and $X^7$ are each individually and independently any amino acid, $Y^1$, $Y^2$, and $Y^3$ are each individually and independently tyrosine, phenylalanine, or phenylglycine, and wherein $Y^1$, $Y^2$, and $Y^3$ are each independently unsubstituted or substituted with —$SO_3H$, —$CH_2SO_3H$, —$CF_2SO_3H$, —$CO_2H$, —$CONH_2$, —$NHSO_2CH_3$, —$SO_2NH_2$, or —$CH_2PO_3H$, wherein at least one of $Y^1$, $Y^2$, and $Y^3$ is substituted with —$CH_2SO_3H$, $Z^1$ is proline or hydroxyproline, and wherein the saccharide or polysaccharide comprises one or more sugars selected from the group consisting of:

2-(acetylamino)-2-deoxy-galactose,
galactose,
2-(acetylamino)-2-deoxy-glucose,
fucose, and
5-acetamido-3,5-dideoxy-glycero-galacto-2-nonulosonic acid.

2. The glycopeptide of claim 1, wherein at least two of $Y^1$, $Y^2$, and $Y^3$ are substituted with —$CH_2SO_3H$.

3. The glycopeptide of claim 1, wherein $Y^1$, $Y^2$, and $Y^3$ are substituted with —$CH_2SO_3H$.

4. The glycopeptide of claim 1, wherein the polysaccharide is sialyl Lewis X or sialyl Lewis A.

5. The glycopeptide of claim 1, wherein the polysaccharide comprises 2-(acetylamino)-2-deoxy-galactose alpha 1 bonded to $W^1$,
galactose beta 3 bonded to 2-(acetylamino)-2-deoxy-galactose,
2-(acetylamino)-2-deoxy-glucose beta 6 bonded to 2-(acetylamino)-2-deoxy-galactose and fucose is alpha 3 bonded to 2-(acetylamino)-2-deoxy-glucose.

6. The glycopeptide of claim 1, wherein the polysaccharide comprises
2-(acetylamino)-2-deoxy-galactose alpha 1 bonded to $W^1$,
galactose beta 3 bonded to 2-(acetylamino)-2-deoxy-galactose,
2-(acetylamino)-2-deoxy-glucose beta 6 bonded to 2-(acetylamino)-2-deoxy-galactose,
fucose is alpha 3 bonded to 2-(acetylamino)-2-deoxy-glucose, and
galactose beta 4 bonded to 2-(acetylamino)-2-deoxy-glucose.

7. The glycopeptide of claim 1, wherein the polysaccharide comprises
2-(acetylamino)-2-deoxy-galactose alpha 1 bonded to $W^1$,
galactose beta 3 bonded to 2-(acetylamino)-2-deoxy-galactose,
2-(acetylamino)-2-deoxy-glucose beta 6 bonded to 2-(acetylamino)-2-deoxy-galactose,
fucose is alpha 3 bonded to 2-(acetylamino)-2-deoxy-glucose,
galactose beta 4 bonded to 2-(acetylamino)-2-deoxy-glucose, and
5-acetamido-3,5-dideoxy-glycero-galacto-2-nonulosonic acid alpha 3 bonded to galactose.

8. The glycopeptide of claim 1, wherein the polysaccharide comprises,
2-(acetylamino)-2-deoxy-galactose alpha 1 bonded to $W^1$,
galactose beta 3 bonded to 2-(acetylamino)-2-deoxy-galactose,
2-(acetylamino)-2-deoxy-glucose beta 6 bonded to 2-(acetylamino)-2-deoxy-galactose,
galactose beta 4 bonded to 2-(acetylamino)-2-deoxy-glucose,
5-acetamido-3,5-dideoxy-glycero-galacto-2-nonulosonic acid alpha 3 bonded to galactose, and
fucose is alpha 3 bonded to 2-(acetylamino)-2-deoxy-glucose.

9. The glycopeptide of claim 1, wherein the polysaccharide comprises,
2-(acetylamino)-2-deoxy-galactose alpha 1 bonded to $W^1$,
a first galactose beta 3 bonded to 2-(acetylamino)-2-deoxy-galactose,
2-(acetylamino)-2-deoxy-glucose beta 6 bonded to 2-(acetylamino)-2-deoxy-galactose,
a second galactose beta 4 bonded to 2-(acetylamino)-2-deoxy-glucose,
fucose is alpha 3 bonded to 2-(acetylamino)-2-deoxy-glucose, and
5-acetamido-3,5-dideoxy-glycero-galacto-2-nonulosonic acid is alpha 3 bonded to the first galactose.

10. The glycopeptide of claim 1, wherein $X^1$, $X^3$, $X^4$, and $X^7$ are each individually and independently E, D, N, or Q.

11. The glycopeptide of claim 1, wherein $X^2$, $X^5$, and $X^6$ are each individually and independently L, I, V, A or F.

12. The glycopeptide of claim 1, wherein the isolated glycopeptide comprises $Y^1EY^2LDY^3DFLZ^1EW^1$, (SEQ ID NO: 2)

$Y^1EY^2LDY^3DFLZ^1EW^1EP$, (SEQ ID NO: 3)

$Y^1EY^2LDY^3DFLZ^1EW^1EPL$, (SEQ ID NO: 4)

$EY^1EY^2LDY^3DFLZ^1EW^1$, (SEQ ID NO: 5)

$EY^1EY^2LDY^3DFLZ^1EW^1E$, (SEQ ID NO: 6)

$EY^1EY^2LDY^3DFLZ^1EW^1EP$, (SEQ ID NO: 7)

$EY^1EY^2LDY^3DFLZ^1EW^1EPL$, (SEQ ID NO: 8)

$KEY^1EY^2LDY^3DFLZ^1EW^1$, (SEQ ID NO: 9)

$KEY^1EY^2LDY^3DFLZ^1EW^1E$, (SEQ ID NO: 10)

$KEY^1EY^2LDY^3DFLZ^1EW^1EP$, or (SEQ ID NO: 11)

$KEY^1EY^2LDY^3DFLZ^1EW^1EPL$. (SEQ ID NO: 12)

13. The glycopeptide of claim 1 selected from $KEY^1EY^2LDY^3DFLZ^1EW^1EPL$ (SEQ ID NO: 12) or salt thereof wherein,
$W^1$ is threonine,
$Y^1$, $Y^2$, and $Y^3$ are phenylalanine 4-substituted with —CH$_2$SO$_3$H,
$Z^1$ is proline,
2-(acetylamino)-2-deoxy-galactose alpha 1 bonded to $W^1$,
galactose beta 3 bonded to 2-(acetylamino)-2-deoxy-galactose, 2-(acetylamino)-2-deoxy-glucose beta 6 bonded to 2-(acetylamino)-2-deoxy-galactose, fucose is alpha 3 bonded to 2-(acetylamino)-2-deoxy-glucose, galactose beta 4 bonded to 2-(acetylamino)-2-deoxy-glucose, and 5-acetamido-3,5-dideoxy-glycero-galacto-2-nonulosonic acid is alpha 3 bonded to galactose.

14. A pharmaceutical composition comprising a glycopeptide of claim 1 and a pharmaceutically acceptable excipient.

15. The pharmaceutical composition of claim 14 in the form of a pill, tablet, capsule, or gel.

16. The pharmaceutical composition of claim 14 in the form of an aqueous saline buffer wherein the pharmaceutically acceptable excipient is a saccharide or polysaccharide.

17. A method of treating or preventing atherosclerosis, atherosclerotic lesions, thrombus formation, thromboembolism, stroke, or myocardial infarction comprising administering an effective amount of a pharmaceutical composition of claim 14 to a subject in need thereof.

18. The method of claim 17 wherein the subject is at risk of, exhibiting symptoms of, or diagnosed with atherosclerosis, atherosclerotic lesions, thrombus formation, thromboembolism, stroke, or myocardial infarction.

19. A method of treating or preventing allergy or lung diseases comprising administering an effective amount of a pharmaceutical composition of claim 14 to a subject in need thereof.

20. The method of claim 17 wherein the subject is at risk of, exhibiting symptoms of, or diagnosed with asthma, bronchitis, emphysema, and COPD.

21. The glycopeptide of claim 1, wherein the isolated glycopeptide comprises $Y^1EY^2LDY^3DFLZ^1EW^1EPL$,  (SEQ ID NO: 4)

$EY^1EY^2LDY^3DFLZ^1EW^1EPL$,  (SEQ ID NO: 8)

$KEY^1EY^2LDY^3DFLZ^1EW^1$,  (SEQ ID NO: 9)

$KEY^1EY^2LDY^3DFLZ^1EW^1E$,  (SEQ ID NO: 10)

$KEY^1EY^2LDY^3DFLZ^1EW^1EP$,  (SEQ ID NO: 11)
or $KEY^1EY^2LDY^3DFLZ^1EW^1EPL$.  (SEQ ID NO: 12)

22. The glycopeptide of claim 1, wherein the isolated glycopeptide comprises $KEY^1EY^2LDY^3DFLZ^1EW^1EPL$ (SEQ ID NO: 12).

23. The glycopeptide of claim 22, wherein $W^1$ is threonine.

24. The glycopeptide of claim 22, wherein $Z^1$ is proline.

* * * * *

UNITED STATES PATENT AND TRADEMARK OFFICE
CERTIFICATE OF CORRECTION

| | |
|---|---|
| PATENT NO. | : 10,253,071 B2 |
| APPLICATION NO. | : 14/895606 |
| DATED | : April 9, 2019 |
| INVENTOR(S) | : Richard D. Cummings et al. |

It is certified that error appears in the above-identified patent and that said Letters Patent is hereby corrected as shown below:

On the Title Page

After item (60) please insert the following section:
--Related U.S. Application Data
(65) Provisional application No. 61/830,285, filed on Jun. 3, 2013.--.

In the Specification

At Column 1, Lines 7-10, the following sentences: "This invention was made with government support under Grants DK069275, HL106018, HL60963, and HL085607 awarded by the National Institutes of Health. The government has certain rights in the invention." should be replaced with:
--This invention was made with government support under Grants DK069275, HL106018, HL060693, and HL085607 awarded by the National Institutes of Health. The government has certain rights in the invention.--.

In the Claims

In Claim 5, at Column 25, Lines 1-2, the text: "fucose is alpha 3 bonded to 2-(acetylamino)-2-deoxy-glucose." should be replaced with the text: --fucose alpha 3 bonded to 2-(acetylamino)-2-deoxy-glucose.--.

In Claim 6, at Column 25, Lines 10-11, the text: "fucose is alpha 3 bonded to 2-(acetylamino)-2-deoxy-glucose, and" should be replaced with the text: --fucose alpha 3 bonded to 2-(acetylamino)-2-deoxy-glucose, and--.

In Claim 8, at Column 25, Lines 38-39, the text: "fucose is alpha 3 bonded to 2-(acetylamino)-2-deoxy-glucose." should be replaced with the text: --fucose alpha 3 bonded to 2-(acetylamino)-2-deoxy-glucose.--.

Signed and Sealed this
Fourth Day of February, 2020

Andrei Iancu
*Director of the United States Patent and Trademark Office*

In Claim 9, at Column 25, Lines 49-52, the text: "fucose is alpha 3 bonded to 2-(acetylamino)-2-deoxy-glucose, and 5-acetamido-3,5-dideoxy-glycero-galacto-2-nonulosonic acid is alpha 3 bonded to the first galactose." should be replaced with the text: --fucose alpha 3 bonded to 2-(acetylamino)-2-deoxy-glucose, and 5-acetamido-3,5-dideoxy-glycero-galacto-2-nonulosonic acid alpha 3 bonded to the first galactose.--.